US010308967B2

(12) United States Patent
Long et al.

(10) Patent No.: US 10,308,967 B2
(45) Date of Patent: Jun. 4, 2019

(54) MILLING PROCESS

(71) Applicant: Novozymes A/S, Bagsvaerd (DK)

(72) Inventors: Zhen Long, Beijing (CN); Wanghui Xu, Beijing (CN); Wang Han, Beijing (CN); Scott R. McLaughlin, Wake Forest, NC (US); Randall Deinhammer, Wake Forest, NC (US); Paria Saunders, Knightdale, NC (US); Bernardo Vidal, Jr., Wake Forest, NC (US); Xinyu Shen, Wake Forest, NC (US); Michael John Akerman, Wake Forest, NC (US); Tom Gibbons, Franklinton, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/033,751

(22) PCT Filed: Nov. 26, 2014

(86) PCT No.: PCT/CN2014/092260
§ 371 (c)(1),
(2) Date: May 2, 2016

(87) PCT Pub. No.: WO2015/078372
PCT Pub. Date: Jun. 4, 2015

(65) Prior Publication Data
US 2016/0257981 A1    Sep. 8, 2016

(30) Foreign Application Priority Data

Nov. 26, 2013  (WO) ............... PCT/CN2013/087861

(51) Int. Cl.
C12P 19/04 (2006.01)
C08B 30/02 (2006.01)
C08B 30/04 (2006.01)
C12N 9/58 (2006.01)
C12N 9/64 (2006.01)

(52) U.S. Cl.
CPC .............. *C12P 19/04* (2013.01); *C08B 30/02* (2013.01); *C08B 30/042* (2013.01); *C08B 30/044* (2013.01); *C08B 30/046* (2013.01); *C12N 9/58* (2013.01); *C12N 9/6408* (2013.01)

(58) Field of Classification Search
None
See application file for complete search history.

(56) References Cited

U.S. PATENT DOCUMENTS

| 5,066,218 A | 11/1991 | Silver |
| 6,566,125 B2 | 5/2003 | Johnston |
| 2003/0092149 A1* | 5/2003 | Olsen .................... C08B 30/042 435/183 |
| 2004/0028775 A1* | 2/2004 | Olsen .................... C08B 30/042 426/52 |
| 2012/0276075 A1* | 11/2012 | Monod ................... C12N 9/62 424/94.2 |
| 2014/0356345 A1* | 12/2014 | Cavaletti ................ A23L 33/10 424/94.63 |
| 2015/0259662 A1* | 9/2015 | Stringer ................. C12N 9/485 426/63 |
| 2016/0002690 A1* | 1/2016 | Long ...................... C12P 19/04 435/99 |
| 2016/0257981 A1* | 9/2016 | Long ...................... C08B 30/02 |

FOREIGN PATENT DOCUMENTS

| WO | 200200731 A1 | 1/2002 |
| WO | 200200911 A1 | 1/2002 |
| WO | 200202644 A1 | 1/2002 |
| WO | 2010/027846 A1 | 3/2010 |
| WO | WO-2012019151 A1 * | 2/2012 ............... C12P 7/10 |
| WO | 2013098185 A1 | 7/2013 |

OTHER PUBLICATIONS

Suzuki et al., "Grifolisin, a member of the sedolisin family produced by the fungus Grifola frondosa", Phytochemistry, vol. 66, pp. 983-990, 2005.*
Catara et al., "A new kumamolisin-like protease from Alicyclobacillus acidocaldarius: an enzyme active under extreme acidic conditions", Biocatalysis and Biotransformation, vol. 24, No. 5, pp. 358-370, 2006.*
K. Oda, "New families of carboxyl peptidases: serine-carboxyl peptidases and glutamic peptidases", The Journal of Biochemistry, vol. 151, No. 1, pp. 13-25, 2012.*
Floudas et al, 2012 Genbank Access No. EIW61051.
Johnston et al, 2004, Cereal Chem. vol. 81, No. 5 pp. 626-632.

* cited by examiner

*Primary Examiner* — Richard C Ekstrom
(74) *Attorney, Agent, or Firm* — Elias Lambiris

(57) ABSTRACT

Provided are processes for treating crop kernels which comprising the steps of a) soaking kernels in water to produce soaked kernels; b) grinding the soaked kernels; c) treating the soaked kernels in the presence of a polypeptide having protease activity.

16 Claims, No Drawings
Specification includes a Sequence Listing.

MILLING PROCESS

CROSS-REFERENCE TO RELATED APPLICATIONS

This application is a 35 U.S.C. 371 national application of PCT/CN2014/092260 filed Nov. 26, 2014, which claims priority or the benefit under 35 U.S.C. 119 of Chinese PCT application no. PCT/CN2013/087861 filed Nov. 26, 2013, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to an improved process of treating crop kernels to provide a starch product of high quality suitable for conversion of starch into mono- and oligosaccharides, ethanol, sweeteners, etc. Further, the invention also relates to an enzyme composition comprising one or more enzyme activities suitable for the process of the invention and to the use of the composition of the invention.

BACKGROUND OF THE INVENTION

Before starch, which is an important constituent in the kernels of most crops, such as corn, wheat, rice, sorghum bean, barley or fruit hulls, can be used for conversion of starch into saccharides, such as dextrose, fructose; alcohols, such as ethanol; and sweeteners, the starch must be made available and treated in a manner to provide a high purity starch. If starch contains more than 0.5% impurities, including the proteins, it is not suitable as starting material for starch conversion processes. To provide such pure and high quality starch product starting out from the kernels of crops, the kernels are often milled, as will be described further below.

Wet milling is often used for separating corn kernels into its four basic components: starch, germ, fiber and protein.

Typically wet milling processes comprise four basic steps. First the kernels are soaked or steeped for about 30 minutes to about 48 hours to begin breaking the starch and protein bonds. The next step in the process involves a coarse grind to break the pericarp and separate the germ from the rest of the kernel. The remaining slurry consisting of fiber, starch and protein is finely ground and screened to separate the fiber from the starch and protein. The starch is separated from the remaining slurry in hydrocyclones. The starch then can be converted to syrup or alcohol, or dried and sold as corn starch or chemically or physically modified to produce modified corn starch.

The use of enzymes has been suggested for the steeping step of wet milling processes. The commercial enzyme product Steepzyme® (available from Novozymes A/S) has been shown suitable for the first step in wet milling processes, i.e., the steeping step where corn kernels are soaked in water.

More recently, "enzymatic milling", a modified wet-milling process that uses proteases to significantly reduce the total processing time during corn wet milling and eliminates the need for sulfur dioxide as a processing agent, has been developed. See Johnston et al., *Cereal Chem,* 81, p. 626-632 (2004).

U.S. Pat. No. 6,566,125 discloses a method for obtaining starch from maize involving soaking maize kernels in water to produce soaked maize kernels, grinding the soaked maize kernels to produce a ground maize slurry, and incubating the ground maize slurry with enzyme (e.g., protease).

U.S. Pat. No. 5,066,218 discloses a method of milling grain, especially corn, comprising cleaning the grain, steeping the grain in water to soften it, and then milling the grain with a cellulase enzyme.

WO 2002/000731 discloses a process of treating crop kernels, comprising soaking the kernels in water for 1-12 hours, wet milling the soaked kernels and treating the kernels with one or more enzymes including an acidic protease.

WO 2002/000911 discloses a process of starch gluten separation, comprising subjecting mill starch to an acidic protease.

WO 2002/002644 discloses a process of washing starch slurry obtained from the starch gluten separation step of a milling process, comprising washing the starch slurry with an aqueous solution comprising an effective amount of acidic protease.

There remains a need for improvement of processes for providing starch suitable for conversion into mono- and oligo-saccharides, ethanol, sweeteners, etc.

SUMMARY OF THE INVENTION

The present invention relates to a process for treating crop kernels, comprising the steps of:
  a) soaking kernels to produce soaked kernels;
  b) grinding the soaked kernels;
  c) treating the soaked kernels in the presence of a polypeptide having protease activity,
wherein step c) is performed before, simultaneously with or after step b),
and said polypeptide is a serine protease of the peptidase family S53 or selected from the group consisting of:
(a) a polypeptide having at least 80%, at least 85%, at least 90%, at least 91%, at least 92%, at least 93%, at least 94%, at least 95%, at least 96%, at least 97%, at least 98%, at least 99% or at least 100% sequence identity to the polypeptide of SEQ ID NO: 5, SEQ ID NO: 6, or the mature polypeptide of SEQ ID NO: 2 or SEQ ID NO: 4;
(b) a polypeptide encoded by a polynucleotide that hybridizes under high stringency conditions, or very high stringency conditions with
(i) the mature polypeptide coding sequence of SEQ ID NO: 1,
(ii) the mature polypeptide coding sequence of SEQ ID NO: 3,
(iii) the full-length complementary strand of (i) or (ii);
(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99%, or at least 100% sequence identity to the mature polypeptide coding sequence of SEQ ID NO: 1 or SEQ ID NO: 3;
(d) a variant of the polypeptide of SEQ ID NO: 5, SEQ ID NO: 6, or the mature polypeptide of SEQ ID NO: 2 or SEQ ID NO: 4 comprising a substitution, deletion, and/or insertion at one or more (several) positions; and
(e) a fragment of a polypeptide of (a), (b), (c) or (d) having protease activity.

In a preferred embodiment the polypeptide having protease activity is a serine protease, such as a serine protease of family S53, such as S53 protease from *Meripilus giganteus*, or S53 protease from *Dichomitus squalens* or *Trametes versicolor*.

In a preferred embodiment the protease comprises or consists of SEQ ID NO: 2, SEQ ID NO: 4, SEQ ID NO: 5 or SEQ ID NO: 6.

In a preferred embodiment the protease comprises or consists of SEQ ID NO: 24 or SEQ ID NO: 25 disclosed in WO 2014/037438.

The present invention also relates to a use of the polypeptides used in a process treating crop for kernels and an enzyme composition comprising the polypeptides used in the present invention.

OVERVIEW OF SEQUENCE LISTING

SEQ ID NO: 1 is the cDNA sequence of S53 protease 3 as isolated from *Meripilus giganteus*.
SEQ ID NO: 2 is the amino acid sequence as deduced from SEQ ID NO: 1.
SEQ ID NO: 3 is the DNA sequence of the recombinant expressed DNA sequence with HQ-tag.
SEQ ID NO: 4 is the amino acid sequence as deduced from SEQ ID NO: 3.
SEQ ID NO: 5 is the amino acid sequence of the mature S53 protease 3 from *Meripilus giganteus*.
SEQ ID NO: 6 is the amino acid sequence of the mature S53 protease obtained from SEQ ID NO. 3.
SEQ ID NO: 7 is primer 597.
SEQ ID NO: 8 is primer 598

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant polynucleotide.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of the polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to additional nucleotides that provide for its expression.

Fragment: The term "fragment" means a polypeptide having one or more (e.g. several) amino acids deleted from the amino and/or carboxyl terminus of a mature polypeptide; wherein the fragment has protease activity. In one aspect, a fragment contains at least 330 amino acid residues (e.g., amino acids 20 to 349 of SEQ ID NO: 2); in another aspect a fragment contains at least 345 amino acid residues (e.g., amino acids 10 to 354 of SEQ ID NO: 2); in a further aspect a fragment contains at least 355 amino acid residues (e.g., amino acids 5 to 359 of SEQ ID NO: 2).

Host cell: The term "host cell" means any cell type that is susceptible to transformation, transfection, transduction, and the like with a nucleic acid construct or expression vector comprising a polynucleotide of the present invention. The term "host cell" encompasses any progeny of a parent cell that is not identical to the parent cell due to mutations that occur during replication.

Isolated polynucleotide: The term "isolated polynucleotide" means a polynucleotide that is modified by the hand of man relative to that polynucleotide as found in nature. In one aspect, the isolated polynucleotide is at least 1% pure, e.g., at least 5% pure, more at least 10% pure, at least 20% pure, at least 40% pure, at least 60% pure, at least 80% pure, at least 90% pure, and at least 95% pure, as determined by agarose electrophoresis. The polynucleotides may be of genomic, cDNA, RNA, semisynthetic, synthetic origin, or any combinations thereof.

Isolated polypeptide: The term "isolated polypeptide" means a polypeptide that is modified by the hand of man relative to that polypeptide as found in nature. In one aspect, the polypeptide is at least 1% pure, e.g., at least 5% pure, at least 10% pure, at least 20% pure, at least 40% pure, at least 60% pure, at least 80% pure, and at least 90% pure, as determined by SDS-PAGE.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 366 in the numbering of SEQ ID NO: 2 based on sequencing using Edman degredation and intact molecular weight analysis of the mature polypeptide with N-terminal HQ-tag. Using the prediction program SignalP (Nielsen et al., 1997, *Protein Engineering* 10: 1-6), amino acids −198 to −182 in the numbering of SEQ ID NO:2 are predicted to be the signal peptide. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having protease activity. In one aspect, the mature polypeptide coding sequence is nucleotides 605 to 1702 in the numbering of SEQ ID NO:1 based on the determination of the mature polypeptide by Edman degradation and intact molecular weight analysis of the mature polypeptide with N-terminal HQ-tag. Furthermore nucleotides 11 to 61 in the numbering of SEQ ID NO:1 are predicted to encode a signal peptide based on the prediction program SignalP (Nielsen et al., 1997, *Protein Engineering* 10: 1-6).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Operably linked: The term "operably linked" means a configuration in which a control sequence is placed at an appropriate position relative to the coding sequence of a polynucleotide such that the control sequence directs the expression of the coding sequence.

Protease activity: The term "protease activity" means proteolytic activity (EC 3.4). There are several protease activity types such as trypsin-like proteases cleaving at the carboxyterminal side of Arg and Lys residues and chymotrypsin-like proteases cleaving at the carboxyterminal side of hydrophobic amino acid residues. Proteases of the invention are serine endopeptidases (EC 3.4.21) with acidic pH-optimum (pH optimum <pH 7).

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment− Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (several) nucleotides deleted from the 5' and/or 3' end of a mature polypeptide coding sequence; wherein the subsequence encodes a fragment having protease activity. In one aspect, a subsequence contains at least 990 nucleotides (e.g., nucleotides 662 to 1651 of SEQ ID NO: 1), e.g., and at least 1035 nucleotides (e.g., nucleotides 632 to 1666 of SEQ ID NO: 1); e.g., and at least 1065 nucleotides (e.g., nucleotides 617 to 1681 of SEQ ID NO: 1).

Substantially pure polynucleotide: The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5' and 3' untranslated regions, such as promoters and terminators. Preferably, the polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. The variants of the present invention have at least 20%, e.g., at least 40%, at least 50%, at least 60%, at least 70%, at least 80%, at least 90%, at least 95%, or at least 100% of the protease activity of the polypeptide of SEQ ID NO: 5, SEQ ID NO: 6, or the mature polypeptide of SEQ ID NO: 2 or SEQ ID NO: 4.

In one aspect, the variant differs by up to 10 amino acids, e.g., 1, 2, 3, 4, 5, 6, 7, 8, 9, or 10, from the mature polypeptide of a SEQ ID NO: as identified herein. In another embodiment, the present invention relates to variants of the mature polypeptide of a SEQ ID NO: herein comprising a substitution, deletion, and/or insertion at one or more (e.g., several) positions. In an embodiment, the number of amino acid substitutions, deletions and/or insertions introduced into the mature polypeptide of a SEQ ID NO: herein is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters*, 149: 152-156; van Tilbeurgh and Claeyssens, 1985, *FEBS Letters*, 187: 283-288; and Tomme et al., 1988, *Eur. J. Biochem.* 170: 575-581. In the present invention, the Tomme et al. method can be used to determine cellobiohydrolase activity.

Cellulolytic enzyme or cellulase: The term "cellulolytic enzyme" or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No. 1 filter paper, microcrystalline cellulose, bacterial cellulose, algal cellulose, cotton, pretreated lignocellulose, etc. The most common total cellulolytic activity assay is the filter paper assay using Whatman No. 1 filter paper as the substrate. The assay was established by the International Union of Pure and Applied Chemistry (IUPAC) (Ghose, 1987, Measurement of cellulase activities, *Pure Appl. Chem.* 59: 257-68).

Cellulosic material: The term "cellulosic material" means any material containing cellulose. Cellulose is a homopolymer of anyhdrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of lignocellulose when used in conjunction with a cellulase or a mixture of cellulases.

Hemicellulolytic enzyme or hemicellulase: The term "hemicellulolytic enzyme" or "hemicellulase" means one or more (e.g., several) enzymes that hydrolyze a hemicellulosic material. See, for example, Shallom, D. and Shoham, Y. Microbial hemicellulases. *Current Opinion In Microbiology*, 2003, 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) data-base. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. In one aspect, a mixture of CELLUCLAST® 1.5 L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 micromole of azurine produced per minute at 37° C., pH 6 from 0.2% AZCL-arabinoxylan as substrate in 200 mM sodium phosphate pH 6 buffer.

Other Definitions

Crop kernels: The term "crop kernels" includes kernels from, e.g., corn (maize), rice, barley, sorghum bean, fruit hulls, and wheat. Corn kernels are exemplary. A variety of corn kernels are known, including, e.g., dent corn, flint corn, pod corn, striped maize, sweet corn, waxy corn and the like.

In an embodiment, the corn kernel is yellow dent corn kernel. Yellow dent corn kernel has an outer covering referred to as the "Pericarp" that protects the germ in the kernels. It resists water and water vapour and is undesirable to insects and microorganisms.

The only area of the kernels not covered by the "Pericarp" is the "Tip Cap", which is the attachment point of the kernel to the cob.

Germ: The "germ" is the only living part of the corn kernel. It contains the essential genetic information, enzymes, vitamins, and minerals for the kernel to grow into a corn plant. In yellow dent corn, about 25 percent of the germ is corn oil. The endosperm covered surrounded by the germ comprises about 82 percent of the kernel dry weight and is the source of energy (starch) and protein for the germinating seed. There are two types of endosperm, soft and hard. In the hard endosperm, starch is packed tightly together. In the soft endosperm, the starch is loose.

Starch: The term "starch" means any material comprised of complex polysaccharides of plants, composed of glucose units that occurs widely in plant tissues in the form of storage granules, consisting of amylose and amylopectin, and represented as $(C_6H_{10}O_5)_n$, where n is any number.

Milled: The term "milled" refers to plant material which has been broken down into smaller particles, e.g., by crushing, fractionating, grinding, pulverizing, etc.

Grind or grinding: The term "grinding" means any process that breaks the pericarp and opens the crop kernel.

Steep or steeping: The term "steeping" means soaking the crop kernel with water and optionally $SO_2$.

Dry solids: The term "dry solids" is the total solids of a slurry in percent on a dry weight basis.

Oligosaccharide: The term "oligosaccharide" is a compound having 2 to 10 monosaccharide units.

Wet milling benefit: The term "wet milling benefit" means one or more of improved starch yield and/or purity, improved gluten yield and/or purity, improved fiber purity, or steep water filtration, dewatering and evaporation, easier germ separation and/or better post-saccharification filtration, and process energy savings thereof.

DETAILED DESCRIPTION OF THE INVENTION

Polypeptides Having Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the eighteen subclasses thereof). The EC number refers to Enzyme Nomenclature 1992 from NC-IUBMB, Academic Press, San Diego, Calif., including supplements 1-5 published in 1994, *Eur. J. Biochem.* 223: 1-5; 1995, *Eur. J. Biochem.* 232: 1-6; 1996, *Eur. J. Biochem.* 237: 1-5; 1997, *Eur. J. Biochem.* 250: 1-6; and 1999, *Eur. J. Biochem.* 264: 610-650 respectively. The nomenclature is regularly supplemented and updated; see e.g. the World Wide Web (WWW) at http://www.chem.qmw.ac.uk/iubmb/enzyme/index.html.

The proteases used in a process of the invention are selected from the group consisting of:
(a) proteases belonging to the EC 3.4.21. enzyme group; and/or
(b) proteases belonging to the EC 3.4.14. enzyme group; and/or
(c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Peptidase family S53 contains acid-acting endopeptidases and tripeptidyl-peptidases. The residues of the catalytic triad are Glu, Asp, Ser, and there is an additional acidic residue, Asp, in the oxyanion hole. The order of the residues is Glu, Asp, Asp, Ser. The Ser residue is the nucleophile equivalent to Ser in the Asp, His, Ser triad of subtilisin, and the Glu of the triad is a substitute for the general base, His, in subtilisin.

Mutation of any of the amino acids of the catalytic triad or oxyanion hole will result in a change or loss of enzyme activity. The amino acids of the catalytic triad and oxyanion hole of the S53 protease 3 from *Meripilus giganteus* (SEQ ID NO: 5) are probably positions Glu-85, Asp-89, Asp-175 and Ser-283. The amino acids of the catalytic triad and oxyanion hole of the S53 protease from *Trametes versicolor* (SEQ ID NO: 24 disclosed in WO2014/037438) are probably positions Glu-85, Asp-89, Asp-175 and Ser-283.

The peptidases of the S53 family tend to be most active at acidic pH (unlike the homologous subtilisins), and this can be attributed to the functional importance of carboxylic residues, notably Asp in the oxyanion hole. The amino acid sequences are not closely similar to those in family S8 (i.e. serine endopeptidase subtilisins and homologues), and this, taken together with the quite different active site residues and the resulting lower pH for maximal activity, provides for a substantial difference to that family. Protein folding of the peptidase unit for members of this family resembles that of subtilisin, having the clan type SB.

A new S53 protease from *Meripilus giganteus* with high activity at low pH (3-4) on wet milling was identified and cloned in relation to the present invention. For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Proteases used in a process of the invention are serine proteases of the peptidase family S53. The proteases exhibit pH properties, especially pH stability properties, which make them of substantial interest as candidates for use in wet milling, and other applications.

The proteases used in a process of the invention are acidic proteases with a preference for hydrophobic amino acid residues such as Leu, Tyr, Phe and Met in the P1 position. The proteases have high activity on Suc-Ala-Ala-Pro-Leu-pNA and Suc-Ala-Ala-Pro-Phe-pNA with a broad pH range from 2-5 and retain more than 95% activity after being subjected for 2 hours to pH as low as 3.

The polypeptides having protease activity used in a process of the invention are selected from the group consisting of:
(a) a polypeptide having at least 80%, at least 85%, at least 90%, at least 91%, at least 92%, at least 93%, at least 94%, at least 95%, at least 96%, at least 97%, at least 98% or at least 99% sequence identity to the polypeptide of SEQ ID NO: 5, SEQ ID NO: 6, or the mature polypeptide of SEQ ID NO: 2 or SEQ ID NO: 4;

(b) a polypeptide encoded by a polynucleotide that hybridizes under high stringency conditions, or very high stringency conditions with
(i) the mature polypeptide coding sequence of SEQ ID NO: 1,
(ii) the mature polypeptide coding sequence of SEQ ID NO: 3,
(iii) the full-length complementary strand of (i) or (ii);
(c) a polypeptide encoded by a polynucleotide having at least 80%, at least 85%, at least 90%, at least 91%, at least 92%, at least 93%, at least 94%, at least 95%, at least 96%, at least 97%, at least 98% or at least 99% sequence identity to the mature polypeptide coding sequence of SEQ ID NO: 1 or SEQ ID NO: 3;
(d) a variant of the polypeptide of SEQ ID NO: 5, SEQ ID NO: 6, or the mature polypeptide of SEQ ID NO: 2 or SEQ ID NO: 4 comprising a substitution, deletion, and/or insertion at one or more (several) positions; and
(e) a fragment of a polypeptide of (a), (b), (c) or (d) having protease activity.

In an embodiment, the protease may be present in an amount of 0.00005-2.5 mg enzyme protein per g dry solids (DS) kernels, preferably 0.0005 to 1.5 mg enzyme protein per g DS kernels, preferably 0.001 to 1 mg enzyme protein per g DS kernels, preferably 0.01 to 0.5 mg enzyme protein per g DS kernels, preferably 0.025 to 0.25 mg enzyme protein per g DS kernels.

In an embodiment, the protease is an acidic protease added in an amount of 1-20,000 HUT/100 g DS kernels, such as 1-10,000 HUT/100 g DS kernels, preferably 300-8,000 HUT/100 g DS kernels, especially 3,000-6,000 HUT/100 g DS kernels, or 4,000-20,000 HUT/100 g DS kernels acidic protease, preferably 5,000-10,000 HUT/100 g, especially from 6,000-16,500 HUT/100 g DS kernels.

In an embodiment, the protease activity is determined using assays described in the "Materials and Methods"-section below, such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

In one embodiment, the polypeptides have at least 20%, e.g., at least 40%, at least 50%, at least 60%, at least 70%, at least 80%, at least 90%, at least 95%, and at least 100% of the protease activity of the polypeptide of SEQ ID NO: 6.

An embodiment of the invention, the polypeptide having protease activity, or a polypeptide encoded by a polynucleotide, has at least 80%, at least 85%, at least 90%, or at least 91% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 92% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 93% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 94% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 95% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 96% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 97% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 98% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has at least 99% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

An embodiment of the invention the polypeptide having protease activity, or a polypeptide encoded by a polynucleotide, has 100% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

In an embodiment of the invention, the polypeptide having protease activity comprise or consists of SEQ ID NO: 2, SEQ ID NO: 4, SEQ ID NO:5 or SEQ ID NO: 6, or the polypeptide of SEQ ID NO: 24 or SEQ ID NO: 25 disclosed in WO 2014/037438.

In one aspect, the polypeptides differ by no more than thirty amino acids, e.g., by twenty five amino acids, by twenty amino acids, by fifteen amino acids, by twelve amino acids, by ten amino acids, by nine amino acids, by eight amino acids, by seven amino acids, by six amino acids, by five amino acids, by four amino acids, by three amino acids, by two amino acids, and by one amino acid from the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

In an embodiment the protease used in a process of the present invention preferably comprises or consists of the amino acid sequence of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438, an allelic variant thereof; or is a fragment missing, e.g. 30, 25, 20, 15, 10 or 5 amino acids from the N- and/or C-terminal and having protease activity. In another aspect, the polypeptide comprises or consists of the polypeptide of SEQ ID NO: 5. In another preferred aspect, the polypeptide comprises or consists of amino acids 1 to 366 of SEQ ID NO: 2.

In an embodiment the polypeptide used in a process of the invention hasprotease activity and are encoded by polynucleotides that hybridize under low stringency conditions, medium stringency conditions, medium-high stringency conditions, high stringency conditions, or very high stringency conditions with (i) the mature polypeptide coding sequence of SEQ ID NO: 1, or (ii) the full-length complementary strand of (i) (J. Sambrook, E. F. Fritsch, and T. Maniatis, 1989, *Molecular Cloning, A Laboratory Manual*, 2d edition, Cold Spring Harbor, N.Y.).

The polynucleotide of SEQ ID NO: 1 or a subsequence thereof, as well as the amino acid sequence of SEQ ID NO: 5, SEQ ID NO: 6, or the mature polypeptide of SEQ ID NO: 2 or SEQ ID NO: 4, or a fragment thereof, may be used to design nucleic acid probes to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H $^{35}$S, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is preferably used in a Southern blot.

For one purpose of the present invention, hybridization indicates that the polynucleotide hybridizes to a labeled nucleic acid probe corresponding to the mature polypeptide coding sequence of SEQ ID NO: 1, its full-length complementary strand or a subsequence thereof under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is a fragment thereof. In another aspect, the nucleic acid probe is a polynucleotide that encodes the polypeptide of SEQ ID NO: 2 or a fragment thereof. In another preferred aspect, the nucleic acid probe is SEQ ID NO: 1.

For long probes of at least 100 nucleotides in length, high to very high stringency conditions are defined as prehybridization and hybridization at 42° C. in 5×SSPE, 0.3% SDS, 200 micrograms/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally. The carrier material is finally washed three times each for 15 minutes using 2×SSC, 0.2% SDS at 65° C. (high stringency), and at 70° C. (very high stringency).

For short probes of about 15 nucleotides to about 70 nucleotides in length, stringency conditions are defined as prehybridization and hybridization at about 5° C. to about 10° C. below the calculated $T_m$ using the calculation according to Bolton and McCarthy (1962, *Proc. Natl. Acad. Sci. USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally. The carrier material is finally washed once in 6×SCC plus 0.1% SDS for 15 minutes and twice each for 15 minutes using 6×SSC at 5° C. to 10° C. below the calculated $T_m$.

In another embodiment, the present invention relates to using variants comprising a substitution, deletion, and/or insertion at one or more (or several) positions of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438, or a homologous sequence thereof. The amino acid changes may be of a minor nature, that is conservative amino acid substitutions, insertions or deletions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tag or HQ-tag, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges that are expected not to alter the specific activity substantially are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/ Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a parent polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identities of essential amino acids can also be inferred from analysis of identities with polypeptides that are related to the parent polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The total number of amino acid substitutions, deletions and/or insertions of the mature polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438 is not more than 20, e.g., 1, 2, 3, 4, 5, 6, 7, 8, 9, 10, 11, 12, 13, 14, 15, 16, 17, 18, 19 or 20.

The polypeptide may be hybrid polypeptide in which a portion of one polypeptide is fused at the N-terminus or the C-terminus of a portion of another polypeptide.

The polypeptide may be a fusion polypeptide or cleavable fusion polypeptide in which another polypeptide is fused at the N-terminus or the C-terminus of the polypeptide of the present invention. A fused polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fused polypeptide is under control of the same promoter(s) and terminator. Fusion proteins may also be constructed using intein technology in which fusions are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

The polypeptide may be expressed by a recombinant DNA sequence containing the coding for a His-tag or HQ-tag to give, after any post-translational modifications, the mature polypeptide containing all or part of the His- or HQ-tag. The HQ-tag, having the sequence -RHQHQHQ, may be fully or partly cleaved off the polypeptide during the post-translational modifications resulting in for example the additional amino acids -RHQHQ attached to the N-terminal of the mature polypeptide.

Carbohydrate molecules are often attached to a polypeptide from a fungal source during post-translational modification. In order to aid mass spectrometry analysis, the polypeptide can be incubated with an endoglycosidase to deglycosylate each N-linked position. For every deglycosylated N-linked site, one N-acetyl hexosamine remains on the protein backbone.

Sources of Polypeptides Having Protease Activity

A polypeptide having protease activity used in accordance with the present invention may be obtained from fungi of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide may be a fungal polypeptide. For example, the polypeptide may be a polypeptide having protease activity from within a phylum such as Basidiomycota. In one aspect, the polypeptide is a protease from a fungus of the class Agaricomycetes, such as from the order Polyporales, or from the family Coriolaceae, or from the genus *Meripilus*. In one embodiment, the polypeptide used in a process of the present invention is from *Meripilus giganteus*.

In one embodiment, the polypeptide used in a process of the present invention is from genus *Dichomitus*, preferably from *Dichomitus squalens*. In one embodiment, the polypeptide used in a process of the present invention is from genus *Trametes*, preferably from *Trametes vericolor*.

It will be understood that the aforementioned species, encompasses both the perfect and imperfect states, and other taxonomic equivalents, e.g., anamorphs, regardless of the species name by which they are known. Those skilled in the art will readily recognize the identity of appropriate equivalents.

Strains of these taxa are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The techniques used to isolate or clone a polynucleotide encoding a polypeptide are known in the art and include isolation from genomic DNA, preparation from cDNA, or a combination thereof. The cloning of the polynucleotides from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus* sp., or another or related organism from the order Bacillales and thus, for example, may be an allelic or species variant of the polypeptide encoding region of the polynucleotide.

In some embodiments, the polynucleotides comprises or consists of polynucleotides having a degree of sequence identity to the mature polypeptide coding sequence of SEQ ID NO: 1 of at least 90%, e.g., at least 91%, at least 92%, at least 93%, at least 94%, at least 95%, at least 96%, at least 97%, at least 98%, at least 99%, or 100%, which encode a polypeptide having protease activity.

Modification of a polynucleotide encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

In embodiments the polynucleotides encoding polypeptides having protease activity hybridize under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the genomic DNA sequence comprising the mature polypeptide coding sequence of SEQ ID NO: 1, or (iii) the full-length complementary strand of (i) or (ii); or allelic variants and subsequences thereof (Sambrook et al., 1989, supra), as defined herein.

In one aspect, the polynucleotide comprises or consists of SEQ ID NO: 1, the mature polypeptide coding sequence of SEQ ID NO: 1, or a subsequence of SEQ ID NO: 1 that encodes a fragment of SEQ ID NO: 2 having protease activity, such as the polynucleotide of nucleotides 605 to 1702 of SEQ ID NO: 1.

The Milling Process

The kernels are milled in order to open up the structure and to allow further processing and to separate the kernels into the four main constituents: starch, germ, fiber and protein.

In one embodiment, a wet milling process is used. Wet milling gives a very good separation of fiber and/or germ and meal (starch granules and protein) and is often applied at locations where there is a parallel production of syrups.

The inventors of the present invention have surprisingly found that the quality of the starch and/or gluten final product may be improved by treating crop kernels in the processes as described herein.

The processes of the invention result in comparison to traditional processes in a higher starch and/or gluten yield and or quality, in that the final starch and gluten product is more pure and/or a higher yield is obtained and/or less process time is used. Another advantage may be that the amount of chemicals, such as SO2 and NaHSO3, which need to be used, may be reduced or even fully removed.

Wet Milling

Starch is formed within plant cells as tiny granules insoluble in water. When put in cold water, the starch granules may absorb a small amount of the liquid and swell. At temperatures up to about 50° C. to 75° C. the swelling may be reversible. However, with higher temperatures an irreversible swelling called "gelatinization" begins. Granular starch to be processed according to the present invention may be a crude starch-containing material comprising (e.g., milled) whole grains including non-starch fractions such as germ residues and fibers. The raw material, such as whole grains, may be reduced in particle size, e.g., by wet milling, in order to open up the structure and allowing for further processing. Wet milling gives a good separation of germ and meal (starch granules and protein) and is often applied at locations where the starch hydrolyzate is used in the production of, e.g., syrups.

In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

More particularly, degradation of the kernels of corn and other crop kernels into starch suitable for conversion of starch into mono- and oligo-saccharides, ethanol, sweeteners, etc. consists essentially of four steps:

1. Steeping and germ separation,
2. Fiber washing and drying,
3. Starch gluten separation, and
4. Starch washing.

1. Steeping and Germ Separation

Corn kernels are softened by soaking in water for between about 30 minutes to about 48 hours, preferably 30 minutes to about 15 hours, such as about 1 hour to about 6 hours at a temperature of about 50° C., such as between about 45° C. to 60° C. During steeping, the kernels absorb water, increasing their moisture levels from 15 percent to 45 percent and more than doubling in size. The optional addition of e.g. 0.1 percent sulfur dioxide (SO2) and/or NaHSO3 to the water prevents excessive bacteria growth in the warm environment. As the corn swells and softens, the mild acidity of the steepwater begins to loosen the gluten bonds within the corn and release the starch. After the corn kernels are steeped they are cracked open to release the germ. The germ contains the valuable corn oil. The germ is separated from the heavier density mixture of starch, hulls and fiber essentially by "floating" the germ segment free of the other substances under closely controlled conditions. This method serves to eliminate any adverse effect of traces of corn oil in later processing steps.

In an embodiment of the invention the kernels are soaked in water for 2-10 hours, preferably about 3-5 hours at a temperature in the range between 40 and 60° C., preferably around 50° C.

In one embodiment, 0.01-1%, preferably 0.05-0.3%, especially 0.1% SO2 and/or NaHSO3 may be added during soaking.

2. Fiber Washing and Drying

To get maximum starch recovery, while keeping any fiber in the final product to an absolute minimum, it is necessary to wash the free starch from the fiber during processing. The fiber is collected, slurried and screened to reclaim any residual starch or protein.

3. Starch Gluten Separation

The starch-gluten suspension from the fiber-washing step, called mill starch, is separated into starch and gluten. Gluten has a low density compared to starch. By passing mill starch through a centrifuge, the gluten is readily spun out.

4. Starch Washing.

The starch slurry from the starch separation step contains some insoluble protein and much of solubles. They have to be removed before a top quality starch (high purity starch) can be made. The starch, with just one or two percent protein remaining, is diluted, washed 8 to 14 times, rediluted and washed again in hydroclones to remove the last trace of protein and produce high quality starch, typically more than 99.5% pure.

Products

Wet milling can be used to produce, without limitation, corn steep liquor, corn gluten feed, germ, corn oil, corn gluten meal, corn starch, modified corn starch, syrups such as corn syrup, and corn ethanol.

Other Enzymes

The enzyme(s) and polypeptides described below are to be used in an "effective amount" in processes of the present invention. Below should be read in context of the enzyme disclosure in the "Definitions"-section above.

Cellulolytic Compositions

In an embodiment the cellulolytic composition is derived from a strain of *Trichoderma*, such as a strain of *Trichoderma reesei*; a strain of *Humicola*, such as a strain of *Humicola insolens*, and/or a strain of *Chrysosporium*, such as a strain of *Chrysosporium lucknowense*.

In a preferred embodiment the cellulolytic composition is derived from a strain of *Trichoderma reesei*.

The cellulolytic composition may comprise one or more of the following polypeptides, including enzymes: GH61 polypeptide having cellulolytic enhancing activity, beta-glucosidase, beta-xylosidase, CBHI and CBHII, endoglucanase, xylanase, or a mixture of two, three, or four thereof.

In an embodiment the cellulolytic composition comprises a GH61 polypeptide having cellulolytic enhancing activity and a beta-glucosidase.

In an embodiment the cellulolytic composition comprises a GH61 polypeptide having cellulolytic enhancing activity and a beta-xylosidase.

In an embodiment, the cellulolytic composition comprises a GH61 polypeptide having cellulolytic enhancing activity and an endoglucanase.

In an embodiment, the cellulolytic composition comprises a GH61 polypeptide having cellulolytic enhancing activity and a xylanase.

In an embodiment, the cellulolytic composition comprises a GH61 polypeptide having cellulolytic enhancing activity, an endoglucanase, and a xylanase.

In an embodiment the cellulolytic composition comprises a GH61 polypeptide having cellulolytic enhancing activity, a beta-glucosidase, and a beta-xylosidase. In an embodiment the cellulolytic composition comprises a GH61 polypeptide having cellulolytic enhancing activity, a beta-glucosidase, and an endoglucanase. In an embodiment the cellulolytic composition comprises a GH61 polypeptide having cellulolytic enhancing activity, a beta-glucosidase, and a xylanase.

In an embodiment the cellulolytic composition comprises a GH61 polypeptide having cellulolytic enhancing activity, a beta-xylosidase, and an endoglucanase. In an embodiment the cellulolytic composition comprises a GH61 polypeptide having cellulolytic enhancing activity, a beta-xylosidase, and a xylanase.

In an embodiment the cellulolytic composition comprises a GH61 polypeptide having cellulolytic enhancing activity, a beta-glucosidase, a beta-xylosidase, and an endoglucanase. In an embodiment the cellulolytic composition comprises a GH61 polypeptide having cellulolytic enhancing activity, a beta-glucosidase, a beta-xylosidase, and a xylanase. In an embodiment the cellulolytic composition comprises a GH61 polypeptide having cellulolytic enhancing activity, a beta-glucosidase, an endoglucanase, and a xylanase.

In an embodiment the cellulolytic composition comprises a GH61 polypeptide having cellulolytic enhancing activity, a beta-xylosidase, an endoglucanase, and a xylanase.

In an embodiment the cellulolytic composition comprises a GH61 polypeptide having cellulolytic enhancing activity, a beta-glucosidase, a beta-xylosidase, an endoglucanase, and a xylanase.

In an embodiment the endoglucanase is an endoglucanase I.

In an embodiment the endoglucanase is an endoglucanase II.

In an embodiment, the cellulolytic composition comprises a GH61 polypeptide having cellulolytic enhancing activity, an endoglucanase I, and a xylanase.

In an embodiment, the cellulolytic composition comprises a GH61 polypeptide having cellulolytic enhancing activity, an endoglucanase II, and a xylanase.

In another embodiment the cellulolytic composition comprises a GH61 polypeptide having cellulolytic enhancing activity, a beta-glucosidase, and a CBHI.

In another embodiment the cellulolytic composition comprises a GH61 polypeptide having cellulolytic enhancing activity, a beta-glucosidase, a CBHI and a CBHII.

The cellulolytic composition may further comprise one or more enzymes selected from the group consisting of an esterase, an expansin, a laccase, a ligninolytic enzyme, a pectinase, a peroxidase, a protease, a swollenin, and a phytase.

GH61 Polypeptide Having Cellulolytic Enhancing Activity

The cellulolytic composition may in one embodiment comprise one or more GH61 polypeptide having cellulolytic enhancing activity.

In one embodiment GH61 polypeptide having cellulolytic enhancing activity, is derived from the genus *Thermoascus*, such as a strain of *Thermoascus aurantiacus*, such as the one described in WO 2005/074656 as Sequence Number 2; or a GH61 polypeptide having cellulolytic enhancing activity having at least 80%, such as at least 85%, such as at least 90%, preferably 95%, such as at least 96%, such as 97%, such as at least 98%, such as at least 99% identity to Sequence Number 2 in WO 2005/074656.

In one embodiment, the GH61 polypeptide having cellulolytic enhancing activity, is derived from a strain derived from *Penicillium*, such as a strain of *Penicillium emersonii*, such as the one disclosed in WO 2011/041397, or a GH61 polypeptide having cellulolytic enhancing activity having at least 80%, such as at least 85%, such as at least 90%, preferably 95%, such as at least 96%, such as 97%, such as at least 98%, such as at least 99% identity to Sequence Number 2 in WO 2011/041397.

In one embodiment the GH61 polypeptide having cellulolytic enhancing activity is derived from the genus *Thielavia*, such as a strain of *Thielavia terrestris*, such as the one described in WO 2005/074647 as Sequence Number 7 and Sequence Number 8; or one derived from a strain of *Aspergillus*, such as a strain of *Aspergillus fumigatus*, such as the one described in WO 2010/138754 as Sequence Number 2, or a GH61 polypeptide having cellulolytic enhancing activity having at least 80%, such as at least 85%, such as at least 90%, preferably 95%, such as at least 96%, such as 97%, such as at least 98%, such as at least 99% identity thereto.

Endoglucanase

In one embodiment, the cellulolytic composition comprises an endoglucanase, such as an endoglucanase I or endoglucanase II.

Examples of bacterial endoglucanases that can be used in the processes of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the present invention, include, but are not limited to, a *Trichoderma reesei* endoglucanase I (Penttila et al., 1986, *Gene* 45: 253-263, *Trichoderma reesei* Cel7B endoglucanase I (GENBANK™ accession no. M15665), *Trichoderma reesei* endoglucanase II (Saloheimo, et al., 1988, *Gene* 63:11-22), *Trichoderma reesei* Cel5A endoglucanase II (GENBANK™ accession no. M19373), *Trichoderma reesei* endoglucanase III (Okada et al., 1988, *Appl. Environ. Microbiol.* 64: 555-563, GENBANK™ accession no. AB003694), *Trichoderma reesei* endoglucanase V (Saloheimo et al., 1994, *Molecular Microbiology* 13: 219-228, GENBANK™ accession no. Z33381), *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Erwinia carotovora* endoglucanase (Saarilahti et al., 1990, *Gene* 90: 9-14), *Fusarium oxysporum* endoglucanase (GENBANK™ accession no. L29381), *Humicola grisea* var. *thermoidea* endoglucanase (GENBANK™ accession no. AB003107), *Melanocarpus albomyces* endoglucanase (GENBANK™ accession no. MAL515703), *Neurospora crassa* endoglucanase (GENBANK™ accession no. XM_324477), *Humicola insolens* endoglucanase V, *Myceliophthora thermophila* CBS 117.65 endoglucanase, basidiomycete CBS 495.95 endoglucanase, basidiomycete CBS 494.95 endoglucanase, *Thielavia terrestris* NRRL 8126 CEL6B endoglucanase, *Thielavia terrestris* NRRL 8126 CEL6C endoglucanase, *Thielavia terrestris* NRRL 8126 CEL7C endoglucanase, *Thielavia terrestris* NRRL 8126 CEL7E endoglucanase, *Thielavia terrestris* NRRL 8126 CEL7F endoglucanase, *Cladorrhinum foecundissimum* ATCC 62373 CEL7A endoglucanase, and *Trichoderma reesei* strain No. VTT-D-80133 endoglucanase (GENBANK™ accession no. M15665).

In one embodiment, the endoglucanase is an endoglucanase II, such as one derived from *Trichoderma*, such as a strain of *Trichoderma reesei*, such as the one described in WO 2011/057140 as Sequence Number 22; or an endoglucanase having at least 80%, such as at least 85%, such as at least 90%, preferably 95%, such as at least 96%, such as 97%, such as at least 98%, such as at least 99% identity to Sequence Number 22 in WO 2011/057140. In one aspect, the protease differs by up to 10 amino acids, e.g., 1, 2, 3, 4, 5, 6, 7, 8, 9, or 10, from the mature polypeptide of Sequence Number 22 in WO 2011/057140. In another embodiment, the present invention relates to variants of the mature polypeptide of Sequence Number 22 in WO 2011/057140 comprising a substitution, deletion, and/or insertion at one or more (e.g., several) positions. In an embodiment, the number of amino acid substitutions, deletions and/or insertions introduced into the mature polypeptide of Sequence Number 22 in WO 2011/057140 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

Xylanase

In one embodiment, the cellulolytic composition comprises a xylanase. In a preferred aspect, the xylanase is a Family 10 xylanase.

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Thielavia terrestris* NRRL 8126 (WO 2009/079210), and *Trichophaea saccata* GH10 (WO 2011/057083).

In one embodiment the GH10 xylanase is derived from the genus *Aspergillus*, such as a strain of *Aspergillus aculeatus*, such as the one described in WO 94/021785 as Sequence Number 5 (referred to as Xyl II); or a GH10 xylanase having at least 80%, such as at least 85%, such as at least 90%, preferably 95%, such as at least 96%, such as 97%, such as at least 98%, such as at least 99% identity to Sequence Number 5 in WO 94/021785. In one aspect, the protease differs by up to 10 amino acids, e.g., 1, 2, 3, 4, 5, 6, 7, 8, 9, or 10, from the mature polypeptide of Sequence Number 5 described in WO 94/021785. In another embodiment, the present invention relates to variants of the mature polypeptide of Sequence Number 5 described in WO 94/021785 comprising a substitution, deletion, and/or insertion at one or more (e.g., several) positions. In an embodiment, the number of amino acid substitutions, deletions and/or insertions introduced into the mature polypeptide of Sequence Number 5 described in WO 94/021785 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

In one embodiment the GH10 xylanase is derived from the genus *Aspergillus*, such as a strain of *Aspergillus fumigatus*, such as described as SEQ ID NO: 6 in WO 2006/078256 as Xyl III, or a GH10 xylanase having at least 80%, such as at least 85%, such as at least 90%, preferably 95%, such as at least 96%, such as 97%, such as at least 98%, such as at least 99% identity to Xyl III in WO 2006/078256. In one aspect, the protease differs by up to 10 amino acids, e.g., 1, 2, 3, 4, 5, 6, 7, 8, 9, or 10, from the mature polypeptide of SEQ ID NO: 6 described in WO 2006/078256. In another embodiment, the present invention relates to variants of the mature polypeptide of SEQ ID NO: 6 described in WO 2006/078256 comprising a substitution, deletion, and/or insertion at one or more (e.g., several) positions. In an embodiment, the number of amino acid substitutions, deletions and/or insertions introduced into the mature polypeptide of SEQ ID NO: 6 described in WO 2006/078256 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

Beta-Xylosidase

Examples of beta-xylosidases useful in the processes of the present invention include, but are not limited to, beta-xylosidases from *Neurospora crassa* (SwissProt accession number Q7SOW4), *Trichoderma reesei* (UniProtKB/TrEMBL accession number Q92458), and *Talaromyces emersonii* (SwissProt accession number Q8X212).

In one embodiment the beta-xylosidase is derived from the genus *Aspergillus*, such as a strain of *Aspergillus fumigatus*, such as the one described in WO 2011/057140 as Sequence Number 206; or a beta-xylosidase having at least 80%, such as at least 85%, such as at least 90%, preferably 95%, such as at least 96%, such as 97%, such as at least 98%, such as at least 99% identity to Sequence Number 206 in WO 2011/057140. In one aspect, the protease differs by up to 10 amino acids, e.g., 1, 2, 3, 4, 5, 6, 7, 8, 9, or 10, from the mature polypeptide of SEQ ID NO: 206 described in WO 2011/057140. In another embodiment, the present invention relates to variants of the mature polypeptide of SEQ ID NO: 206 described in WO 2011/057140 comprising a substitution, deletion, and/or insertion at one or more (e.g., several) positions. In an embodiment, the number of amino acid substitutions, deletions and/or insertions introduced into the mature polypeptide of SEQ ID NO: 206 described in WO 2011/057140 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function.

In one embodiment the beta-xylosidase is derived from a strain of the genus *Aspergillus*, such as a strain of *Aspergillus fumigatus*, such as the one disclosed in U.S. provisional 61/526,833 or PCT/US12/052163 (Examples 16 and 17), or derived from a strain of *Trichoderma*, such as a strain of *Trichoderma reesei*, such as the mature polypeptide of Sequence Number 58 in WO 2011/057140 or a beta-xylosidase having at least 80%, such as at least 85%, such as at least 90%, preferably 95%, such as at least 96%, such as 97%, such as at least 98%, such as at least 99% identity thereto.

Beta-Glucosidase

The cellulolytic composition may in one embodiment comprise one or more beta-glucosidase. The beta-glucosidase may in one embodiment be one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as such as one disclosed in WO 2005/047499 or an *Aspergillus fumigatus* beta-glucosidase variant, such as one disclosed in PCT application PCT/US11/054185 (or U.S. provisional application No. 61/388,997), such as one with the following substitutions: F100D, S283G, N456E, F512Y.

In one embodiment the beta-glucosidase is derived from the genus *Aspergillus*, such as a strain of *Aspergillus fumigatus*, such as the one described in WO 2005/047499, or a beta-glucosidase having at least 80%, such as at least 85%, such as at least 90%, preferably 95%, such as at least 96%, such as 97%, such as at least 98%, such as at least 99% identity thereto.

In one embodiment the beta-glucosidase is derived from the genus *Aspergillus*, such as a strain of *Aspergillus fumigatus*, such as the one described in WO 2012/044915, or a beta-xylosidase having at least 80%, such as at least 85%, such as at least 90%, preferably 95%, such as at least 96%, such as 97%, such as at least 98%, such as at least 99% identity thereto.

Cellobiohydrolase I

The cellulolytic composition may in one embodiment may comprise one or more CBH I (cellobiohydrolase I). In one embodiment the cellulolytic composition comprises a cellobiohydrolase I (CBHI), such as one derived from a strain of the genus *Aspergillus*, such as a strain of *Aspergillus fumigatus*, such as the Cel7A CBHI disclosed in Sequence Number 2 in WO 2011/057140, or a strain of the genus *Trichoderma*, such as a strain of *Trichoderma reesei*.

In one embodiment the cellobiohydrolyase I is derived from the genus *Aspergillus*, such as a strain of *Aspergillus fumigatus*, such as the one described in WO 2011/057140, or a CBHI having at least 80%, such as at least 85%, such as at least 90%, preferably 95%, such as at least 96%, such as 97%, such as at least 98%, such as at least 99% identity thereto.

Cellobiohydrolase II

The cellulolytic composition may in one embodiment comprise one or more CBH II (cellobiohydrolase II). In one embodiment the cellobiohydrolase II (CBHII), such as one derived from a strain of the genus *Aspergillus*, such as a strain of *Aspergillus fumigatus*, or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

In one embodiment the cellobiohydrolase II is derived from the genus *Aspergillus*, such as a strain of *Aspergillus fumigatus*, such as the one described in WO 2011/057140, or a CBHII having at least 80%, such as at least 85%, such as at least 90%, preferably 95%, such as at least 96%, such as 97%, such as at least 98%, such as at least 99% identity thereto.

Exemplary Cellulolytic Compositions

As mentioned above the cellulolytic composition may comprise a number of different polypeptides, such as enzymes.

In an embodiment, the cellulolytic composition comprises a *Trichoderma reesei* cellulase preparation containing *Aspergillus oryzae* beta-glucosidase fusion protein (e.g. SEQ ID NO: 74 or 76 in WO 2008/057637) and *Thermoascus aurantiacus* GH61A polypeptide (e.g., SEQ ID NO: 2 in WO 2005/074656).

In an embodiment, the cellulolytic composition comprises a blend of an *Aspergillus aculeatus* GH10 xylanase (e.g., SEQ ID NO: 5 (Xyl II) in WO 94/021785) and a *Trichoderma reesei* cellulase preparation containing *Aspergillus fumigatus* beta-glucosidase (e.g., SEQ ID NO: 2 in WO 2005/047499) and *Thermoascus aurantiacus* GH61A polypeptide (e.g., SEQ ID NO: 2 in WO 2005/074656).

In an embodiment, the cellulolytic composition comprises a blend of an *Aspergillus fumigatus* GH10 xylanase (e.g., SEQ ID NO: 6 (Xyl III) in WO 2006/078256) and *Aspergillus fumigatus* beta-xylosidase (e.g., SEQ ID NO: 206 in WO 2011/057140) with a *Trichoderma reesei* cellulase preparation containing *Aspergillus fumigatus* cellobiohydrolase I (e.g., SEQ ID NO: 6 in WO 2011/057140), *Aspergillus fumigatus* cellobiohydrolase II (e.g., SEQ ID NO: 18 in WO 2011/057140), *Aspergillus fumigatus* beta-glucosidase variant (e.g., one having F100D, S283G, N456E, F512Y substitutions disclosed in WO 2012/044915), and *Penicillium* sp. (*emersonii*) GH61 polypeptide (e.g., SEQ ID NO: 2 in WO 2011/041397).

In an embodiment the cellulolytic composition comprises a *Trichoderma reesei* cellulolytic enzyme composition, further comprising *Thermoascus aurantiacus* GH61A polypeptide having cellulolytic enhancing activity (e.g., SEQ ID NO: 2 in WO 2005/074656) and *Aspergillus oryzae* beta-glucosidase fusion protein (e.g., SEQ ID NO: 74 or 76 in WO 2008/057637).

In another embodiment the cellulolytic composition comprises a *Trichoderma reesei* cellulolytic enzyme composition, further comprising *Thermoascus aurantiacus* GH61A polypeptide having cellulolytic enhancing activity (e.g., SEQ ID NO: 2 in WO 2005/074656) and *Aspergillus fumigatus* beta-glucosidase (e.g., SEQ ID NO: 2 in WO 2005/047499).

In another embodiment the cellulolytic composition comprises a *Trichoderma reesei* cellulolytic enzyme composition, further comprising *Penicillium emersonii* GH61A polypeptide having cellulolytic enhancing activity disclosed as, e.g., SEQ ID NO: 2 in WO 2011/041397, *Aspergillus fumigatus* beta-glucosidase (e.g., SEQ ID NO: 2 in WO 2005/047499) or a variant thereof with the following substitutions: F100D, S283G, N456E, F512Y.

The enzyme composition of the present invention may be in any form suitable for use, such as, for example, a crude fermentation broth with or without cells removed, a cell lysate with or without cellular debris, a semi-purified or purified enzyme composition, or a host cell, e.g., *Trichoderma* host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Enzymatic Amount

In particular embodiments, the protease is present in the enzyme composition in a range of about 5% w/w to about 65% w/w of the total amount of enzyme protein. In other embodiments, the protease is present in about 5% w/w to about 60% w/w, about 5% w/w to about 50% w/w, about 5% w/w to about 40% w/w, about 5% w/w to about 30% w/w, about 10% w/w to about 30% w/w, or about 10% w/w to about 20% w/w.

Enzymes may be added in an effective amount, which can be adjusted according to the practitioner and particular process needs. In general, enzyme may be present in an amount of 0.0001-2.5 mg total enzyme protein per g dry solids (DS) kernels, preferably 0.001-1 mg enzyme protein per g DS kernels, preferably 0.0025-0.5 mg enzyme protein per g DS kernels, preferably 0.025-0.25 mg enzyme protein per g DS kernels, preferably 0.05-0.125 mg enzyme protein per g DS kernels. In particular embodiments, the enzyme may be present in an amount of, e.g. 2.5 µg, 12.5 µg, 25 µg, 50 µg, 75 µg, 100 µg, 125 µg, 150 µg, 175 µg, 200 µg, 250 µg, 500 µg enzyme protein per g DS kernels.

Other Enzyme Activities

According to the invention an effective amount of one or more of the following activities may also be present or added during treatment of the kernels: pentosanase, pectinase, arabinanase, arabinofurasidase, xyloglucanase, phytase activity.

It is believed that after the division of the kernels into finer particles the enzyme(s) can act more directly and thus more efficiently on cell wall and protein matrix of the kernels. Thereby the starch is washed out more easily in the subsequent steps.

Preferred Embodiments

The following embodiments of the invention are exemplary.

1. A process for treating crop kernels, comprising the steps of:
a) soaking kernels to produce soaked kernels;
b) grinding the soaked kernels;
c) treating the soaked kernels in the presence of a polypeptide having protease activity,
wherein step c) is performed before, simultaneously with or after step b),
and said polypeptide is a serine protease of the peptidase family S53 or selected from the group consisting of:
(a) a polypeptide having at least 80% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438;
(b) a polypeptide encoded by a polynucleotide that hybridizes under high stringency conditions, or very high stringency conditions with
(i) the mature polypeptide coding sequence of SEQ ID NO: 1,
(ii) the mature polypeptide coding sequence of SEQ ID NO: 3,
(iii) the full-length complementary strand of (i) or (ii);
(c) a polypeptide encoded by a polynucleotide having at least 80% sequence identity to the mature polypeptide coding sequence of SEQ ID NO: 1 or SEQ ID NO: 3;

(d) a variant of the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438 comprising a substitution, deletion, and/or insertion at one or more (several) positions; and (e) a fragment of a polypeptide of (a), (b), (c), or (d) having protease activity.

2. The process of embodiment 1, wherein the said polypeptide is a polypeptide having at least 85%, at least 90%, at least 91%, at least 92%, at least 93%, at least 94%, at least 95%, at least 96%, at least 97%, at least 98%, at least 99% or at least 100% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438.

3. The process of embodiment 1, wherein the said polypeptide is a polypeptide encoded by a polynucleotide having at least 85%, at least 90%, at least 95%, at least 96%, at least 97%, at least 98%, at least 99% or at least 100% sequence identity to the mature polypeptide coding sequence of SEQ ID NO: 1 or SEQ ID NO: 3.

4. The process of embodiment 1, wherein the said polypeptide having protease activity comprising or consisting of SEQ ID NO: 2, SEQ ID NO: 4, SEQ ID NO: 5 or SEQ ID NO: 6, or the polypeptide of SEQ ID NO: 24 or SEQ ID NO: 25 disclosed in WO 2014/037438.

5. The process of any of the preceding embodiments, wherein the polypeptide having protease activity is a serine protease, such as a serine protease of family S53, such as S53 protease 3 from *Meripilus giganteus*, S53 protease from *Dichomitus squalens* or S53 protease from *Trametes vericolor*.

6. The process of any of the preceding embodiments, wherein the said polypeptide having protease activity is from the genus *Meripilus*, preferably is from *Meripilus giganteus*, or the said polypeptide having protease activity is from the genus *Dichomitus*, preferably is from *Dichomitus squalens*, or the said polypeptide having protease activity is from genus *Trametes*, preferably is from *Trametes vericolor*.

7. The process of any of the preceding embodiments, further comprising treating the soaked kernels in the presence of a beta-xylosidase.

8. The process of any of the preceding embodiments, further comprising treating the soaked kernels in the presence of a cellulase and/or a hemicellulase.

9. The process of any of the preceding embodiments, further comprising treating the soaked kernels in the presence of a xylanase.

10. The process of any of the preceding embodiments, further comprising treating the soaked kernels in the presence of a cellulolytic composition comprising: 1) a cellulase or a hemicellulase, and 2) a GH61 polypeptide.

11. The process of any of the preceding embodiments, further comprising treating the soaked kernels in the presence of an acetylxylan esterase.

12. The process of any of the preceding embodiments, further comprising treating the soaked kernels in the presence of an enzyme selected from the group consisting of an endoglucanase, a xylanase, a cellobiohydrolase I, a cellobiohydrolase II, a GH61 polypeptide, or a combination thereof.

13. The process of any of the preceding embodiments, wherein said polypeptide is present in an amount of preferably 0.0005 to 1.5 mg enzyme protein per g DS kernels, preferably 0.001 to 1 mg enzyme protein per g DS kernels, preferably 0.01 to 0.5 mg enzyme protein per g DS kernels, preferably 0.025 to 0.25 mg enzyme protein per g DS kernels.

14. The process of any of the preceding embodiments, wherein the crop kernels are from corn (maize), rice, barley, sorghum bean, or fruit hulls, or wheat.

15. An enzyme composition comprising a polypeptide having protease activity, wherein said polypeptide is selected from the group consisting of:

(a) a polypeptide having at least 80%, at least 85%, at least 90%, at least 91%, at least 92%, at least 93%, at least 94%, at least 95%, at least 96%, at least 97%, at least 98%, at least 99% or at least 100%, sequence identity to the polypeptide of SEQ ID NO: 5, SEQ ID NO: 6, or the mature polypeptide of SEQ ID NO: 2 or SEQ ID NO: 4;

(b) a polypeptide encoded by a polynucleotide that hybridizes under high stringency conditions, or very high stringency conditions with (i) the mature polypeptide coding sequence of SEQ ID NO: 1, (ii) the mature polypeptide coding sequence of SEQ ID NO: 3, (iii) the full-length complementary strand of (i) or (ii);

(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99%, or at least 100% sequence identity to the mature polypeptide coding sequence of SEQ ID NO: 1 or SEQ ID NO: 3;

(d) a variant of the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438 comprising a substitution, deletion, and/or insertion at one or more (several) positions; and (e) a fragment of a polypeptide of (a), (b), (c) or (d) having protease activity.

16. The composition of embodiment 15, wherein the said polypeptide having protease activity comprising or consisting of SEQ ID NO: 2, SEQ ID NO: 4, SEQ ID NO: 5 or SEQ ID NO: 6, or the polypeptide of SEQ ID NO: 24 or SEQ ID NO: 25 disclosed in WO 2014/037438.

17. The composition of embodiment 15 or 16, wherein the polypeptide having protease activity is a serine protease, such as a serine protease of family S53, such as S53 protease 3 from *Meripilus giganteus*.

18. The composition of any of embodiments 15-17, wherein the said polypeptide having protease activity is from the genus *Meripilus*, preferably is from *Meripilus giganteus*.

19. The composition of any of embodiments 15-18 further comprising of an enzyme selected from the group consisting of a beta-xylosidase, a cellulase, a hemicelluase, a xylanase, an endoglucanase, a GH61 polypeptide, or a combination thereof.

20. The composition of any of embodiments 15-19 further comprising a beta-xylosidase, a xylanase and an endoglucanase.

21. Use of a serine protease of the peptidase family S53 or a polypeptide having protease activity or an enzyme composition of any of embodiments 15-20 in a process of any of the preceding embodiments 1-14, wherein said polypeptide is selected from the group consisting of:

(a) a polypeptide having at least 80%, at least 85%, at least 90%, at least 91%, at least 92%, at least 93%, at least 94%, at least 95%, at least 96%, at least 97%, at least 98%, at least 99%, or at least 100% sequence identity to the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438;

(b) a polypeptide encoded by a polynucleotide that hybridizes under high stringency conditions, or very high stringency conditions with (i) the mature polypeptide coding sequence of SEQ ID NO: 1, (ii) the mature polypeptide coding sequence of SEQ ID NO: 3, (iii) the full-length complementary strand of (i) or (ii);

(c) a polypeptide encoded by a polynucleotide having at least 80%, at least 85%, at least 90%, at least 91%, at least 92%, at least 93%, at least 94%, at least 95%, at least 96%, at least 97%, at least 98%, at least 99%, or at least 100% sequence identity to the mature polypeptide coding sequence of SEQ ID NO: 1 or SEQ ID NO: 3;

(d) a variant of the polypeptide of SEQ ID NO: 5, SEQ ID NO: 6, or the mature polypeptide of SEQ ID NO: 2 or SEQ ID NO: 4, or the polypeptide of SEQ ID NO: 24 or SEQ ID NO: 25 disclosed in WO 2014/037438 comprising a substitution, deletion, and/or insertion at one or more (several) positions; and (e) a fragment of a polypeptide of (a), (b), (c) or (d) having protease activity.

22. The use of embodiment 21, wherein the said polypeptide having protease activity comprising or consisting of SEQ ID NO: 2, SEQ ID NO: 4, SEQ ID NO: 5 or SEQ ID NO: 6, or the polypeptide of SEQ ID NO: 24 or SEQ ID NO: 25 disclosed in WO 2014/037438.

23. The use of any of embodiments 21-22, wherein the polypeptide having protease activity is a serine protease, such as a serine protease of family S53, such as S53 protease 3 from *Meripilus giganteus*, S53 protease from *Dichomitus squalens* or S53 protease from *Trametes vericolor*.

24. The use of any of embodiments 21-23, wherein the said polypeptide having protease activity is from the genus *Meripilus*, preferably is from *Meripilus giganteus*, or the said polypeptide having protease activity is from the genus *Dichomitus*, preferably is from *Dichomitus squalens*, or the said polypeptide having protease activity is from genus *Trametes*, preferably is from *Trametes vericolor*.

EXAMPLES

Materials and Methods

Enzymes

Protease I: Acidic protease from *Aspergillus aculeatus*, CBS 101.43 disclosed in WO 95/02044.

Protease A: A metalloprotease from *Thermoascus aurantiacus* (AP025) having the mature amino acid sequence shown as amino acids 1-177 SEQ ID NO: 2 in WO2003/048353-A1.

Protease B: *Rhizomucor miehei* derived aspartic endopeptidase produced in *Aspergillus oryzae* (Novoren™) available from Novozymes A/S, Denmark.

Protease 3 M.g.: S53 protease 3 from *Meripilus giganteus* prepared as disclosed in Examples 1 and 2 below and available from Novozymes A/S, Denmark.

Protease C: A S53 protease from *Dichomitus squalens* having the amino acid sequence shown as SEQ ID NO: 25 in WO 2014/037438.

Protease D: A S53 protease from *Trametes versicolor* having the mature amino acid sequence shown as SEQ ID NO: 24 in WO 2014/037438.

Cellulase F: A *Trichoderma reesei* cellulolytic enzyme composition containing *Aspergillus fumigatus* GH10 xylanase (SEQ ID NO: 6 (Xyl III) in WO 2006/078256) and *Aspergillus fumigatus* beta-xylosidase (SEQ ID NO: 16 in WO 2013/028928).

Strain

The strain *Meripilus giganteus* was isolated from a fruiting body collected in Denmark in 1993 by Novozymes.

Methods

Determination of Protease HUT Activity:

1 HUT is the amount of enzyme which, at 40° C. and pH 4.7 over 30 minutes forms a hydrolysate from digesting denatured hemoglobin equivalent in absorbency at 275 nm to a solution of 1.10 µg/ml tyrosine in 0.006 N HCl which absorbency is 0.0084. The denatured hemoglobin substrate is digested by the enzyme in a 0.5 M acetate buffer at the given conditions. Undigested hemoglobin is precipitated with trichloroacetic acid and the absorbance at 275 nm is measured of the hydrolysate in the supernatant.

Protease Assays

Kinetic Suc-AAPF-pNA Assay:

pNA substrate: Suc-AAPF-pNA (Bachem L-1400).

Temperature: Room temperature (25° C.)

Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease sample (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

Endpoint Suc-AAPF-pNA Assay:

pNA substrate: Suc-AAPF-pNA (Bachem L-1400).

Temperature: controlled (assay temperature).

Assay buffer: 100 mM succinic acid, 100 mM HEPES, 100 mM CHES, 100 mM CABS, 1 mM $CaCl_2$, 150 mM KCl, 0.01% Triton X-100, pH 4.0

200 µl pNA substrate (50 mg dissolved in 1.0 ml DMSO and further diluted 45× with the Assay buffer) were pipetted in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath and adding 600 µl 500 mM $H_3BO_3$/NaOH, pH 9.7. The tube was mixed and 200 µl mixture was transferred to a microtiter plate, which was read at $OD_{405}$. A buffer blind was included in the assay (instead of enzyme). $OD_{405}$(Sample)–$OD_{405}$(Blind) was a measure of protease activity.

Protazyme AK Assay:

Substrate: Protazyme AK tablet (cross-linked and dyed casein; from Megazyme)

Temperature: controlled (assay temperature).

Assay buffer: 100 mM succinic acid, 100 mM HEPES, 100 mM CHES, 100 mM CABS, 1 mM $CaCl_2$, 150 mM KCl, 0.01% Triton X-100, pH 6.5.

A Protazyme AK tablet was suspended in 2.0 ml 0.01% Triton X-100 by gentle stirring. 500 µl of this suspension and 500 µl assay buffer were dispensed in an Eppendorf tube and placed on ice. 20 µl protease sample (diluted in 0.01% Triton X-100) was added. The assay was initiated by transferring the Eppendorf tube to an Eppendorf thermomixer, which was set to the assay temperature. The tube was incubated for 15 minutes on the Eppendorf thermomixer at its highest shaking rate (1400 rpm.). The incubation was stopped by transferring the tube back to the ice bath. Then the tube was centrifuged in an ice cold centrifuge for a few minutes and 200 µl supernatant was transferred to a microtiter plate, which was read at $OD_{650}$. A buffer blind was included in the assay (instead of enzyme). $OD_{650}$(Sample)–$OD_{650}$(Blind) was a measure of protease activity.

Kinetic Suc-AAPX-pNA Assay:

pNA substrates: Suc-AAPA-pNA (Bachem L-1775)
    Suc-AAPR-pNA (Bachem L-1720)
    Suc-AAPD-pNA (Bachem L-1835)
    Suc-AAPI-pNA (Bachem L-1790)
    Suc-AAPM-pNA (Bachem L-1395)
    Suc-AAPV-pNA (Bachem L-1770)
    Suc-AAPL-pNA (Bachem L-1390)
    Suc-AAPE-pNA (Bachem L-1710)
    Suc-AAPK-pNA (Bachem L-1725)
    Suc-AAPF-pNA (Bachem L-1400)

Temperature: Room temperature (25° C.)

Assay buffer: 100 mM succinic acid, 100 mM HEPES, 100 mM CHES, 100 mM CABS, 1 mM $CaCl_2$, 150 mM KCl, 0.01% Triton X-100, pH 4.0 or pH 9.0.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{405}$ was monitored as a measure of the protease activity.

o-Phthaldialdehyde (OPA) Assay:

This assay detects primary amines and hence cleavage of peptide bonds by a protease can be measured as the difference in absorbance between a protease treated sample and a control sample. The assay is conducted essentially according to Nielsen et al. (Nielsen, P M, Petersen, D, Dampmann, C. Improved method for determining food protein degree of hydrolysis. J Food Sci, 2001, 66: 642-646).

500 µl of sample is filtered through a 100 kDa Microcon centrifugal filter (60 min, 11,000 rpm, 5° C.). The samples are diluted appropriately (e.g. 10, 50 or 100 times) in deionizer water and 25 µl of each sample is loaded into a 96 well microtiter plate (5 replicates). 200 µl OPA reagent (100 mM di-sodium tetraborate decahydrate, 3.5 mM sodium dodecyl sulphate (SDS), 5.7 mM di-thiothreitol (DDT), 6 mM o-phthaldialdehyde) is dispensed into all wells, the plate is shaken (10 sec, 750 rpm) and absorbance measured at 340 nm.

Example 1: Recombinant Expression of the S53 Protease 3 from *Meripilus giganteus* (SEQ ID NO: 3)

In order to obtain material for testing and characterization of the S53 Protease 3 from *Meripilus giganteus*, the DNA sequence from SEQ ID NO: 1 was cloned in an *Aspergillus* expression vector and expressed in *Aspergillus oryzae*.

The S53 Protease 3 gene from *Meripilus giganteus* was sub-cloned into the *Aspergillus* expression vector pMStr100 (WO 10/009400) by amplifying the coding region without the stop codon of the DNA in Seq ID NO: 1 from the cDNA plasmid clone, pA2PR22, with standard PCR techniques using the following primers:

597   TAGGGATCCTCACGATGGTCGCCACCAGCT(SEQ ID NO: 7)

598   CAGGCCGACCGCGGTGAG          (SEQ ID NO: 8)

The PCR product was restricted with BamHI and ligated into the BamHI and NruI sites of pMStr100, resulting in an in-frame fusion with the C-terminal tag sequence RHQHQHQH(stop) in the expression vector. The S53 Protease 3 gene in the resulting *Aspergillus* expression construct, pMStr121, was sequenced, and the protease coding portion of the sequence was confirmed to agree with the original coding sequence of SEQ ID NO: 1. The in-frame fusion to the tag encoding sequence was also confirmed, resulting in the sequence in SEQ ID NO: 3, which encodes the peptide sequence in SEQ ID NO: 4.

The *Aspergillus oryzae* strain BECh2 (WO 00/39322) was transformed with pMStr121 using standard techniques as described by Christensen et al., 1988, Biotechnology 6, 1419-1422 and WO 04/032648. To identify transformants producing the recombinant protease, the transformants and BECh2 were cultured in 10 ml of YP+2% glucose medium at 30° C. and 200RPM. Samples were taken after 3 days growth and resolved with SDS-PAGE to identify recombinant protease production. A novel band between 35 and 50 kDa was observed in cultures of transformants that was not observed in cultures of the untransformed BECh2. Several transformants that appeared to express the recombinant protease at high levels were further cultured in 100 ml of YP+2% glucose medium in 500 ml shake flasks at 30° C. and 200RPM. Samples were taken after 2, 3, and 4 days growth and expression levels compared by resolving the samples with SDS-PAGE. A single transformant that expressed the recombinant protease at relatively high levels was selected and designated EXP01737. EXP01737 was isolated twice by dilution streaking conidia on selective medium containing 0.01% TRITON® X-100 to limit colony size and fermented in YP+2% glucose medium in shake flasks as described above to provide material for purification. The shake flask cultures were harvested after 4 days growth and fungal mycelia was removed by filtering the fermentation broth through Miracloth (Calbiochem) then purified as described in example 2.

YP+2% Glucose Medium
    10 g yeast extract
    20 g peptone
    water to 1 L
    autoclave at 121° C., 20 minutes
    add 100 ml 20% sterile glucose solution Example 2: Purification of the S53 Protease 3 from *Meripilus giganteus* with N-Terminal HQ-Tag The culture broth was centrifuged (20000×g, 20 min) and the supernatant was carefully decanted from the precipitate. The supernatant was filtered through a Nalgene 0.2 µm filtration unit in order to remove the rest of the *Aspergillus* host cells. The 0.2 µm filtrate was transferred to 10 mM Succinic acid/NaOH, pH 3.5 on a G25 Sephadex column (from GE Healthcare). The G25 sephadex transferred enzyme was applied to a Q-sepharose FF column (from GE Healthcare) equilibrated in 10 mM Succinic acid/NaOH, pH 3.5. The run-through and wash with 10 mM Succinic acid/NaOH, pH 3.5 was collected and contained the S53 protease (activity confirmed using the Kinetic Suc-AAPF-pNA assay at pH 4). The pH of the run-through and wash fraction was adjusted to pH 3.25 with 1M HCl while mixing the fraction thoroughly. The pH-adjusted solution was applied to a SP-sepharose FF column (from GE Healthcare) equilibrated in 10 mM Succinic acid/NaOH, pH 3.25. After washing the column extensively with the equilibration buffer, the protease was eluted with a linear NaCl gradient (0→0.5M) in the same buffer over ten column volumes. Fractions from the column were analysed for protease activity (using the Kinetic Suc-AAPF-pNA assay at pH 4) and peak-fractions were pooled. Solid ammonium sulphate was added to the pool to 2.0M final $(NH_4)_2SO_4$ concentration. The enzyme solution was applied to a Phenyl-Toyopearl column (from TosoHaas) equilibrated in 10 mM Succinic acid/NaOH, 2.0M $(NH_4)_2SO_4$, pH 3.25. After washing the column extensively with the equilibration buffer, the S53 protease was eluted with a linear gradient between the equilibration buffer and 10 mM Succinic acid/NaOH, pH 3.25 over ten column volumes. Fractions from the column were analysed for protease activity (using the Kinetic Suc-AAPF-pNA assay at pH 4). Fractions with high activity were pooled and transferred to 10 mM Succinic acid/NaOH, pH 3.5 on a G25 sephadex column (from GE Healthcare). The G25 sephadex transferred protease was applied to a SP-sepharose HP column (from GE Healthcare) equilibrated in 10 mM Succinic acid/NaOH, pH 3.5. After washing the column extensively with the equilibration buffer, the protease was eluted with a linear NaCl gradient (0→0.5M) in the same buffer over five column volumes. Fractions constituting the major peak from the column were pooled as the purified product. The purified product was analysed by SDS-PAGE and one major band was seen on the gel and three minor bands. EDMAN N-terminal sequencing of the bands showed that all the bands were related to the S53 protease and therefore we expect that the minor bands represents nicking of some of the S53 protease molecules. The purified product was used for further characterization.

Example 3: Characterization of the S53 Protease 3 from *Meripilus giganteus* with N-Terminal HQ-Tag The Kinetic Suc-AAPF-pNA assay was used for obtaining the pH-activity profile and the pH-stability profile (residual activity after 2 hours at indicated pH-values). For the pH-stability profile the protease was diluted 10× in the different assay buffers to reach the pH-values of these buffers and then incubated for 2 hours at 37° C. After incubation, the pH of the protease incubations was transferred to the same pH-value, before assay for residual activity, by dilution in the pH 4.0 Assay buffer. The Endpoint Suc-AAPF-pNA assay was used for obtaining the temperature-activity profile at pH 4.0. The Kinetic Suc-AAPX-pNA assay and ten different Suc-AAPX-pNA substrates were used for obtaining the P1-specificity of the enzyme at pH 4.0.

The results are shown in tables 1-4 below. Data for Protease 10R which is disclosed as Protease 10R in WO 2014/037438 are included in the tables. For table 1, the activities are relative to the optimal pH for the enzymes. For table 2, the activities are residual activities relative to samples, which were kept at stable conditions (5° C., pH 4.0 for the S53 protease from example 2; 5° C., pH 9.0 for Protease 10R). For table 3, the activities are relative to the optimal temperature for the enzyme (pH 4.0 for the S53 protease from example 2; pH 6.5 for Protease 10R). For table 4, the activities are relative to the best substrate for the enzymes (Suc-AAPL-pNA for the S53 protease from example 2). The Protazyme AK assay was used for obtaining the temperature-activity profile at pH 6.5 for Protease 10R.

TABLE 1 pH-activity profile at 25° C. as determined using the kinetic Suc-AAPF-pNA assay

| pH | S53 protease from example 2 | Protease 10R |
|---|---|---|
| 2 | 0.38 | — |
| 3 | 0.95 | 0.00 |
| 4 | 1.00 | 0.02 |
| 5 | 0.27 | 0.07 |
| 6 | 0.02 | 0.21 |
| 7 | 0.00 | 0.44 |
| 8 | 0.00 | 0.67 |
| 9 | 0.00 | 0.88 |
| 10 | 0.00 | 1.00 |
| 11 | 0.00 | 0.93 |

TABLE 2 pH-stability profile (residual activity after 2 hours at 37° C.) as determined using the kinetic Suc-AAPF-pNA assay

| pH | S53 protease from example 2 | Protease 10R |
|---|---|---|
| 2 | 0.01 | 0.78 |
| 3 | 0.99 | 1.03 |
| 4 | 0.96 | 0.99 |
| 5 | 0.94 | 1.00 |
| 6 | 0.87 | 1.03 |
| 7 | 0.69 | 1.01 |
| 8 | 0.01 | 0.98 |
| 9 | 0.01 | 0.99 |
| 10 | 0.01 | 0.99 |
| 11 | 0.01 | 0.86 |
| After 2 hours at 5° C. | 1.00 (at pH 4) | 1.00 (at pH 9) |

TABLE 3

Temperature activity profile at pH 4.0 or pH 6.5 as determined using the endpoint Suc-AAPF-pNA assay

| Temp (° C.) | S53 protease from example 2 (pH 4) | Protease 10R (pH 6.5) |
|---|---|---|
| 15 | 0.07 | 0.01 |
| 25 | 0.23 | 0.02 |
| 37 | 0.58 | 0.06 |
| 50 | 1.00 | 0.13 |
| 60 | 0.44 | 0.35 |
| 70 | 0.08 | 0.96 |
| 80 | — | 1.00 |
| 90 | — | 0.18 |

TABLE 4

P1-specificity on 10 Suc-AAPX-pNA substrates at pH 4.0 or pH 9.0 at 37° C. as determined using the kinetic Suc-AAPX-pNA assay

| Suc-AAPX-pNA | S53 protease from example 2 (pH 4) | Protease 10R (pH 9) |
|---|---|---|
| Suc-AAPA-pNA | 0.01 | 0.13 |
| Suc-AAPR-pNA | 0.00 | 0.09 |
| Suc-AAPD-pNA | 0.06 | 0.00 |
| Suc-AAPI-pNA | 0.00 | 0.00 |
| Suc-AAPM-pNA | 0.53 | 0.78 |
| Suc-AAPV-pNA | 0.00 | 0.01 |
| Suc-AAPL-pNA | 1.00 | 0.18 |

TABLE 4-continued

P1-specificity on 10 Suc-AAPX-pNA substrates at pH 4.0 or pH 9.0 at 37° C. as determined using the kinetic Suc-AAPX-pNA assay

| Suc-AAPX-pNA | S53 protease from example 2 (pH 4) | Protease 10R (pH 9) |
|---|---|---|
| Suc-AAPE-pNA | 0.05 | 0.00 |
| Suc-AAPK-pNA | 0.00 | 0.08 |
| Suc-AAPF-pNA | 0.99 | 1.00 |

Other Characteristics for the S53 Protease from Example 2

Determination of the N-terminal sequence was: AIPAS-CASTI.

The relative molecular weight as determined by SDS-PAGE was approx. $M_r$=43 kDa.

Confirmation of N-Terminal HQ-Tag Attached to Mature Sequence

This sample was buffer exchanged with 50 mM sodium acetate buffer pH 5.5 using a vivaspin ultrafiltration unit fitted with a 10 KD cut off filter. Following buffer exchange, 2 µL of endoglycosidase H was added and the sample was then incubated at 5° C. overnight. Note: For every deglycosylated N-linked site one N-acetyl hexosamine remains on the protein backbone increasing the molecular weight with 203.19 Da per site. The sample was then analysed by mass-spectrometry.

The molecular weight determined by intact molecular weight analysis of the major peak was: 38088.6 Da, corresponding to the mature sequence plus -RHQHQ and a single acetyl hexosamine.

The molecular weight determined by intact molecular weight analysis of the secondary peak was: 37961 Da, corresponding to the mature sequence plus -RHQH and a single acetyl hexosamine.

The mature sequence (from EDMAN N-terminal sequencing data and intact molecular weight analysis):

(SEQ ID NO: 6)
AIPASCASTITPACLQAIYGIPTTKATQSSNKLAVSGFIDQFANKADLKS

FLAQFRKDISSSTTFSLQTLDGGENDQSPSEAGIEANLDIQYTVGLATGV

PTTFISVGDDFQDGNLEGFLDIINFLLGESNPPQVLTTSYGQNENTISAK

LANQLCNAYAQLGARGTSILFASGDGGVSGSQSAHCSNFVPTFPSGCPFM

TSVGATQGVSPETAAAFSSGGFSNVFGIPSYQASAVSGYLSALGSTNSGK

FNRSGRGFPDVSTQGVDFQIVSGGQTIGVDGTSCASPTFASVISLVNDRL

IAAGKSPLGFLNPFLYSSAGKAALNDVTSGSNPGCSTNGFPAKAGWDPVT

GLGTPNFAKLLTAVGLRHQHQ.

The calculated molecular weight from this mature sequence is 37882.6 Da.

Example 4: Wet Milling in the Presence of S53 Protease 3 M.g. From Example 2

Treatments of corn were put through a simulated corn wet milling process according to the procedure below. Two treatments involved application of S53 protease from example 2. (Steep B and Steep C) whereas one treatment was enzyme-free (Steep A).

For the enzyme treated steeps (Steeps B and Steep C), a steep solution containing 0.06% (w/v) SO2 and 0.5% (w/v) lactic acid was assembled. 100 grams of dry regular (yellow dent) corn was cleaned to remove the broken kernels and put into 200 mL of the steep water described above for each flask. All flasks were then put into an orbital air heated shaker machine which was set to 52° C. with mild shaking and allowed to mix at this temperature for 16 hours. After 16 hours, all flasks were removed from the air shaker.

The enzyme-free control steep (Steep A) was made up in a similar fashion; with the exception being that it was steeped in a 0.15% (w/v) SO2 and 0.5% (w/v) lactic acid solution, and was steeped for 28 hours prior to grinding.

The corn mixture was poured over a Buchner funnel to dewater it, and 100 mL of fresh tap water was then added to the original steeping flask and swirled for rinsing purpose. It was then poured over the corn as a wash and captured in the same flask as the original corn draining. The purpose of this washing step was to retain as many of the solubles with the filtrate as possible. The filtrate containing solubles was called "light steep water" ("LSW"). The total light steep water fraction collected was then oven-dried to determine the amount of dry substance present. The drying was done by overnight drying in oven set by 105° C.

The corn was then placed into a Waring Laboratory Blender with the blades reversed (so the leading edge was dull). 200 mL of water was added to the corn in the blender, and the corn was then ground for one minute at low speed setting to facilitate germ release. Once ground, the slurry was transferred back to flasks for enzymatic incubation step. 50 mL fresh water was used to rinse the blender and the wash water was added to the flask as well. The enzyme treatment flasks (Steep B and Steep C) were dosed with enzyme and returned to orbital shaker to be incubated at 52° C. for another 4 hours at higher mixing rate. The enzyme dosing was carried out as shown below in Table 5.

TABLE 5

Experimental Design (doses applied per gram of corn dry substance)

| Steep | A | B | C |
|---|---|---|---|
| Enzyme Used | Control (No Enzyme) | Protease 3 M.g. | Protease 3 M.g. |
| Total Enzyme (µg) | 0 | 25 | 125 |

After incubation, the slurry was transferred to a large beaker for released germ removal. The control steep did not go through this incubation step but was ground and then processed immediately as described below.

For degermination, a slotted spoon was used to gently stir the mixture briefly. After the stirring was stopped, large quantities of germ pieces floated to the surface. These were skimmed off of the liquid surface manually using the slotted spoon. The germ pieces were placed on a US No. 100 (150 µm) screen with a catch pan underneath of it. This process of mixing and skimming was repeated until negligible amounts of germ floated up to the surface for skimming. Inspection of the slurry mash in the slotted spoon also showed no evidence of large germ quantities left in the mixture at this point, so de-germination was stopped. The germ pieces that had been accumulated on the No. 100 screen were then added to a flask where they were combined with 125 mL of fresh water, and swirled to simulate a germ wash tank. The contents of the flask were then poured over the screen again, making sure to tap the flask and fully clear it of germ. The de-germinated slurry in the skimming beaker was then poured back into the blender, and the germ wash water in the catch pan underneath of the screen was used to rinse the germ beaker to the blender. Another 125 mL of fresh water was then used to conduct a second rinse of the beaker and was added to the blender. The washed germ on the screen was oven dried overnight at 105° C. prior to analysis.

The fiber, starch, and gluten slurry that had been degerminated was then ground in the blender for 3 minutes at high speed. This increased speed was employed to release as much starch and gluten from the fiber as possible. The resulting ground slurry in the blender was screened over a No. 100 vibrating screen (Retsch Model AS200 sieve shaking unit) with a catch pan underneath. The shaking frequency on the Retsch unit was set to roughly 60 HZ. Once filtration had stopped, the starch and gluten filtrate (called "mill starch") in the catch pan was transferred into a flask until further processing. The fiber on the screen was then slurried in 500 mL of fresh water and then re-poured over the vibrating screen to wash the unbound starch off of the fiber. Again, the starch and gluten filtrate in the catch pan was added to the previous mill starch flask.

The fiber was then washed and screened in this manner three successive times, each time using 240 mL of fresh wash water. This was then followed by a single 125 mL wash while vibrating to achieve maximum starch and gluten liberation from the fiber fraction. After all washings were complete, the fiber was gently pressed on the screen to dewater it before it was transferred to an aluminum weighing pan for oven drying at 105° C. (overnight). All of the filtrate from the washings and pressing was added to the mill starch flask.

The starch and gluten compromising the mill starch was then vacuum filtered through a Buchner Funnel through a Whatman filter paper before being oven dried. The total filtrate volume from the vacuum flask was measured. 250 ml filtrate was transferred to a plastic bottle for oven drying at 105° C. for 48 hours. The total soluble solid content of this fraction was calculated by multiplying the volume of gluten solution by total solids of gluten filtrate. The filter cake was transferred to a stainless steel dish to dry overnight first at 50° C. to minimize the gelatinization and then 105° C. overnight to obtain the dry weight (starch and gluten yield). Tables 6 show the different faction yields in both experiments.

TABLES 6

Fraction yields for experimental control and protease in Experiment 4.

| Steep | A | B | C |
|---|---|---|---|
| Enzyme Used | Control (No Enzyme) | Protease 3 M.g. 25 μg | Protease 3 M.g. 125 μg |
| Starch plus Gluten | 75.26% | 75.73% | 76.34% |
| Fiber | 11.16% | 9.96% | 9.32% |
| Germ | 5.47% | 5.37% | 5.40% |
| LSW Solubles | 4.80% | 3.41% | 3.67% |
| Filtrate Solubles | 1.52% | 3.74% | 4.66% |

Note:
A is average of two batches of experimental data

Example 5: Wet Milling in the Presence of S53 Protease 3 M.g. And Cellulase F

Treatments of corn were put through a simulated corn wet milling process according to the procedure below. Two treatments involved application of the combination of protease and Cellulase F (Steep B and Steep C) whereas one treatment was enzyme-free (Steep A), wherein S53 protease is from example 2. For the enzyme treated steeps (Steep B and Steep C), a steep solution containing 0.06% (w/v) SO2 and 0.5% (w/v) lactic acid was assembled. 100 grams of dry regular (yellow dent) corn was cleaned to remove the broken kernels and put into 200 mL of the steep water described above for each flask. All flasks were then put into an orbital air heated shaker machine which was set to 52° C. with mild shaking and allowed to mix at this temperature for 16 hours. After 16 hours, all flasks were removed from the air shaker. The enzyme-free control steep (Steep A) was made up in a similar fashion; with the exception being that it was steeped in a 0.15% (w/v) SO2 and 0.5% (w/v) lactic acid solution, and was steeped for 28 hours prior to grinding.

The corn mixture was poured over a Buchner funnel to dewater it, and 100 mL of fresh tap water was then added to the original steeping flask and swirled for rinsing purpose. It was then poured over the corn as a wash and captured in the same flask as the original corn draining. The purpose of this washing step was to retain as many of the solubles with the filtrate as possible. The filtrate containing solubles was called "light steep water" ("LSW"). The total light steep water fraction collected was then oven-dried to determine the amount of dry substance present. The drying was done by overnight drying in oven set by 105° C.

The corn was then placed into a Waring Laboratory Blender with the blades reversed (so the leading edge was dull). 200 mL of water was added to the corn in the blender, and the corn was then ground for one minute at low speed setting to facilitate germ release. Once ground, the slurry was transferred back to flasks for enzymatic incubation step. 50 mL fresh water was used to rinse the blender and the wash water was added to the flask as well. The enzyme treatment flasks (Steeps B, and Steep C) were dosed with enzyme and returned to orbital shaker to be incubated at 52° C. for another 4 hours at higher mixing rate. The enzyme dosing was carried out as shown below in Table 7.

TABLE 7

Experimental Design (doses applied per gram of corn dry substance)

| Steep | A | B | C |
|---|---|---|---|
| Enzyme Used | Control (No Enzyme) | Protease I Cellulase F | Protease 3 M.g. Cellulase F |
| μg Protease | 0 | 2.5 | 2.5 |
| μg Cellulase F | 0 | 25 | 25 |

After incubation, the slurry was transferred to a large beaker for released germ removal. The control steep did not go through this incubation step but was ground and then processed immediately as described below.

For degermination, a slotted spoon was used to gently stir the mixture briefly. After the stirring was stopped, large quantities of germ pieces floated to the surface. These were skimmed off of the liquid surface manually using the slotted spoon. The germ pieces were placed on a US No. 100 (150 μm) screen with a catch pan underneath of it. This process of mixing and skimming was repeated until negligible amounts of germ floated up to the surface for skimming. Inspection of the slurry mash in the slotted spoon also showed no evidence of large germ quantities left in the mixture at this point, so de-germination was stopped. The germ pieces that had been accumulated on the No. 100 screen were then added to a flask where they were combined with 125 mL of fresh water, and swirled to simulate a germ wash tank. The contents of the flask were then poured over the screen again, making sure to tap the flask and fully clear it of germ. The de-germinated slurry in the skimming beaker was then poured back into the blender, and the germ wash water in the catch pan underneath of the screen was used to rinse the germ beaker to the blender. Another 125 mL of fresh water was then used to conduct a second rinse of the beaker and was added to the blender. The washed germ on the screen was oven dried overnight at 105° C. prior to analysis.

The fiber, starch, and gluten slurry that had been de-germinated was then ground in the blender for 3 minutes at high speed. This increased speed was employed to release as much starch and gluten from the fiber as possible. The resulting ground slurry in the blender was screened over a No. 100 vibrating screen (Retsch Model AS200 sieve shaking unit) with a catch pan underneath. The shaking frequency on the Retsch unit was set to roughly 60 HZ. Once filtration had stopped, the starch and gluten filtrate (called "mill starch") in the catch pan was transferred into a flask until further processing. The fiber on the screen was then slurried in 500 mL of fresh water and then re-poured over the vibrating screen to wash the unbound starch off of the fiber. Again, the starch and gluten filtrate in the catch pan was added to the previous mill starch flask.

The fiber was then washed and screened in this manner three successive times, each time using 240 mL of fresh wash water. This was then followed by a single 125 mL wash while vibrating to achieve maximum starch and gluten liberation from the fiber fraction. After all washings were complete, the fiber was gently pressed on the screen to dewater it before it was transferred to an aluminum weighing pan for oven drying at 105° C. (overnight). All of the filtrate from the washings and pressing was added to the mill starch flask.

The starch and gluten slurry was then vacuum filtered through a Buchner Funnel through a Whatman filter paper before being oven dried. The total filtrate volume from the vacuum flask was measured. 250 ml filtrate was transferred to a plastic bottle for oven drying at 105° C. for 48 hours. The total soluble solid content of this fraction was calculated by multiplying the volume of gluten solution by total solids of gluten filtrate. The filter cake was transferred to a stainless steel dish to dry overnight first at 50° C. to minimize the gelatinization and then 105° C. overnight to obtain the dry weight. Tables 8 show the different faction yields in both experiments.

TABLES 8

Fraction yields for experimental control and all blends in Experiment 5.

| Steep | A | B | C |
|---|---|---|---|
| Enzyme Used | Control (No Enzyme) | Protease I Cellulase F | Protease 3 M.g. Cellulase F |
| Starch plus Gluten | 75.26% | 76.05% | 76.81% |
| Fiber | 11.16% | 10.15% | 9.52% |
| Germ | 5.47% | 5.58% | 5.53% |
| LSW Solubles | 4.80% | 3.45% | 3.49% |
| Filtrate Solubles | 1.52% | 2.68% | 3.12% |

Note:
A is average of two batches of experimental data;
B is average of four batches of experimental data;
C is average of two batches of experimental data

Example 6: Fiber Washing in the Presence of Different Proteases

Four treatments (Tests A, B, C and D) of the pressed fiber from plant were put through a simulated fiber washing process according to the procedure below.

Mix 10 g (dry weight) pressed fiber from plant with 200 mL pH 3.8 (adjusted with lactic acid) water. Add enzymes as table below and incubate at 52 C for 1 h.

TABLE 9

Protease dosing plan

| Test | A | B | C | D |
|---|---|---|---|---|
| 50 μg Protease | Control (No Enzyme) | Protease 3 M.g. | Protease A | Protease B |

Separate fiber pieces and starch/gluten slurry on 75 um sieve with a catch pan underneath and squeeze fiber manually with a flat scraper to dewater. Once the filtration had stopped, the starch and gluten filtrate in the catch pan was transferred into a mill starch and gluten flask until further processing. The fiber on the screen was then slurried in 200 ml of fresh water and then re-poured over the sieve to wash the unbound starch and protein off the fiber. Again, the starch and gluten filtrate in the catch pan was added to the previous mill starch and gluten flask. The fiber was then washed and screened in this manner two more successive times, each time using 200 mL of fresh wash water.

After all washings were complete, the fiber was gently pressed on the screen to dewater it before it was transferred to an aluminum weighing pan for oven drying at 105° C. (overnight). All of the filtrate from the washings and pressing was added to the mill starch and gluten flask.

The mill starch and gluten was filtered using a Buchner funnel, and the resulting solids cake, along with the filter paper was placed into a pre-weighed dish at 50° C. overnight prior to being dried in a 105° C. oven overnight as well. After complete oven drying, each of the fractions was weighed to obtain a dry matter weight.

Table 10 below shows the product yields (percent of dry solids of each fraction per 5 g dry matter of corn) and residual starch content in fiber for control and enzymatic runs. The results showed that protease 3 M.g. could release more starch and gluten from fiber compared to the conventional process and other proteases.

TABLE 10

Fraction yields for experimental control and all enzymatic treatment (Dry mass of total fiber dry weight %)

| Test | A | B | C | D |
|---|---|---|---|---|
| 50 μg Protease | Control (No Enzyme) | Protease 3 M.g. | Protease A | Protease B |
| Fiber (%) | 76.70% ± 1.70% | 73.35% ± 0.78% | 72.50% ± 0.28% | 72.45% ± 0.35% |
| Starch and gluten (%) | 5.15% ± 0.21% | 6.30% ± 0.42% | 5.75% ± 0.07% | 5.50% ± 0.14% |

Example 7: Fiber Washing in the Presence of Blends with Different S53 Protease and Cellulase Five treatments (Tests A, B, C and D) of the pressed fiber from plant were put through a simulated fiber washing process according to the procedure below.

Mix 5 g (dry weight) pressed fiber from plant with 100 mL 0.05M pH 4.0 acetate sodium buffer. Add enzymes as table below and incubate at 52 C for 4 h.

TABLE 11

Protease dosing plan

| Test | A | B | C | D |
|---|---|---|---|---|
| 2.5 µg Protease | Control (No enzyme) | Protease 3 M.g. | Protease C | Protease D |
| 22.5 µg Cellulase | Control (No enzyme) | Cellulase | Cellulase | Cellulase |

Separate fiber pieces and starch/gluten slurry on 75 um sieve with a catch pan underneath and squeeze fiber manually with a flat scraper to dewater. Once the filtration had stopped, the starch and gluten filtrate in the catch pan was transferred into a mill starch and gluten flask until further processing. The fiber on the screen was then slurried in 100 ml of fresh water and then re-poured over the sieve to wash the unbound starch and protein off the fiber. Again, the starch and gluten filtrate in the catch pan was added to the previous mill starch and gluten flask. The fiber was then washed and screened in this manner two more successive times, each time using 100 mL of fresh wash water.

After all washings were complete, all of the filtrate from the washings and pressing was added to the mill starch and gluten flask. The mill starch and gluten was filtered using a Buchner funnel, and the resulting solids cake, along with the filter paper was placed into a pre-weighed dish at 50° C. overnight prior to being dried in a 105° C. oven overnight as well. After complete oven drying, each of the fractions was weighed to obtain a dry matter weight.

Table 12 below shows the insoluble yields (starch and gluten) of the filtrate (percent of dry solids of each fraction per 5 g dry matter of corn) for control and enzymatic runs. The results showed that all the S53 proteases could release more starch and gluten from fiber compared to the conventional process.

TABLE 12

Insoluble yields for experimental control and all enzymatic treatment (Dry mass of total fiber dry weight %)

| Test | A | B | C | D |
|---|---|---|---|---|
| Insolubles (%) | 10.44% ± 0.35% | 14.68% ± 0.35% | 13.64% ± 0.35% | 14.26% ± 0.35% |

The invention claimed is:

1. A process for treating crop kernels, comprising the steps of:
   a) soaking kernels to produce soaked kernels;
   b) grinding the soaked kernels;
   c) treating the soaked kernels in the presence of a polypeptide having protease activity, wherein step c) is performed before, simultaneously with or after step b),
   and said polypeptide is selected from the group consisting of:
   (a) a polypeptide having at least 90% sequence identity to the polypeptide of SEQ ID NO: 5, SEQ ID NO: 6, or the mature polypeptide of SEQ ID NO: 2 or SEQ ID NO: 4; and (b) a polypeptide encoded by a polynucleotide having at least 90% sequence identity to the mature polypeptide coding sequence of SEQ ID NO: 1 or SEQ ID NO: 3.

2. The process of claim 1, wherein the said polypeptide is a polypeptide having at least 95% sequence identity to the polypeptide of SEQ ID NO: 5, SEQ ID NO: 6, or the mature polypeptide of SEQ ID NO: 2 or SEQ ID NO: 4.

3. The process of claim 1, wherein the polypeptide is a polypeptide encoded by a polynucleotide having at least 95% sequence identity to the mature polypeptide coding sequence of SEQ ID NO: 1 or SEQ ID NO: 3.

4. The process of claim 1, wherein the polypeptide having protease activity comprises or consists of SEQ ID NO: 2, SEQ ID NO: 4, SEQ ID NO: 5 or SEQ ID NO: 6.

5. The process of claim 1, wherein the polypeptide having protease activity is from the genus *Meripilus*, genus *Dichomitus*, or genus *Trametes*.

6. The process of claim 1, further comprising treating the soaked kernels in the presence of a beta-xylosidase.

7. The process of claim 1, further comprising treating the soaked kernels in the presence of a cellulase and/or a hemicelluase.

8. The process of claim 1, further comprising treating the soaked kernels in the presence of a xylanase.

9. The process of claim 1, further comprising treating the soaked kernels in the presence of a cellulolytic composition comprising: 1) a cellulase or a hemicellulase, and 2) a GH61 polypeptide.

10. The process of claim 1, further comprising treating the soaked kernels in the presence of an acetylxylan esterase.

11. The process of claim 1, further comprising treating the soaked kernels in the presence of an enzyme selected from the group consisting of an endoglucanase, a xylanase, a cellobiohydrolase I, a cellobiohydrolase II, a GH61 polypeptide, and combinations thereof.

12. The process of claim 1, wherein said polypeptide is present in an amount of 0.0005 to 1.5 mg enzyme protein per g DS kernels.

13. The process of claim 1, wherein the crop kernels are from corn, maize, rice, barley, sorghum, bean, fruit hulls, or wheat.

14. The process of claim 12, wherein said polypeptide is present in an amount of 0.001 to 1 mg enzyme protein per g DS kernels.

15. The process of claim 12, wherein said polypeptide is present in an amount of 0.01 to 0.5 mg enzyme protein per g DS kernels.

16. The process of claim 1, wherein said polypeptide is present in an amount of 0.025 to 0.25 mg enzyme protein per g DS kernels.

* * * * *

SEQUENCE LISTING

<160> NUMBER OF SEQ ID NOS: 8

<210> SEQ ID NO 1
<211> LENGTH: 1847
<212> TYPE: DNA
<213> ORGANISM: Meripilus giganteus
<220> FEATURE:
<221> NAME/KEY: CDS
<222> LOCATION: (11)..(1702)
<220> FEATURE:
<221> NAME/KEY: sig_peptide
<222> LOCATION: (11)..(61)
<220> FEATURE:
<221> NAME/KEY: mat_peptide
<222> LOCATION: (605)..(1702)

<400> SEQUENCE: 1

```
ctcgaacacg atg gtc gcc acc  agc ttg ctc gtt gcc  tcc cta ttc acg        49
            Met Val Ala Thr Ser Leu Leu Val Ala  Ser Leu Phe Thr
                -195                    -190 ctc gcc ctc ggc acg ccg  acg ggt cgc aac ctc  aag ctg cac gag            94
Leu Ala Leu Gly Thr Pro  Thr Gly Arg Asn Leu  Lys Leu His Glu
-185               -180                   -175 gcg cgc gaa gac ctt cct  gcc ggt ttc tcg ctg  cgc ggc gcc gcc           139
Ala Arg Glu Asp Leu Pro  Ala Gly Phe Ser Leu  Arg Gly Ala Ala
-170               -165                   -160 tcg ccc gac acg acg ctg  aag ctc cgc atc gcg  ctc gtg cag aac           184
Ser Pro Asp Thr Thr Leu  Lys Leu Arg Ile Ala  Leu Val Gln Asn
-155               -150                   -145 aac ttc gcc gag ctc gaa  gac aag ctc tac gac  gtc agc aca ccg           229
Asn Phe Ala Glu Leu Glu  Asp Lys Leu Tyr Asp  Val Ser Thr Pro
-140               -135                   -130 tcc agc gcc aac tac ggc  aac cac ctc tcg aag  gaa gag gtt gag           274
Ser Ser Ala Asn Tyr Gly  Asn His Leu Ser Lys  Glu Glu Val Glu
-125               -120                   -115 cag tac att gct ccg gct  ccc gag agc gtg aaa  gcc gtg aat gcc           319
Gln Tyr Ile Ala Pro Ala  Pro Glu Ser Val Lys  Ala Val Asn Ala
-110               -105                   -100
```

| | | | | | | | | | | | | | | | |
|---|---|---|---|---|---|---|---|---|---|---|---|---|---|---|---|
| tgg | ctc | acc | gag | aac | gga | ctc | gac | gcg | cac | acc | att | tcg | ccc | gcc | ggc | 367 |
| Trp | Leu | Thr | Glu | Asn | Gly | Leu | Asp | Ala | His | Thr | Ile | Ser | Pro | Ala | Gly | |
| -95 | | | | -90 | | | | -85 | | | | | | -80 | | |
| gac | tgg | ctc | gca | ttc | gag | gtc | ccc | gtc | agc | aag | gcg | aat | gag | ctc | ttc | 415 |
| Asp | Trp | Leu | Ala | Phe | Glu | Val | Pro | Val | Ser | Lys | Ala | Asn | Glu | Leu | Phe | |
| | | | | -75 | | | | | -70 | | | | | -65 | | |
| gac | gcc | gac | ttc | tcc | gtg | ttt | acc | cac | gat | gag | tcc | ggc | ctc | gag | gct | 463 |
| Asp | Ala | Asp | Phe | Ser | Val | Phe | Thr | His | Asp | Glu | Ser | Gly | Leu | Glu | Ala | |
| | | -60 | | | | | -55 | | | | | -50 | | | | |
| atc | cgg | acg | ctg | gcc | tac | tcc | atc | cct | gct | gag | ctt | cag | gga | cac | ctc | 511 |
| Ile | Arg | Thr | Leu | Ala | Tyr | Ser | Ile | Pro | Ala | Glu | Leu | Gln | Gly | His | Leu | |
| | | -45 | | | | -40 | | | | | -35 | | | | | |
| gac | ctt | gtt | cac | ccc | acc | gtc | acg | ttc | ccg | aac | ccc | aat | gcg | cac | ctg | 559 |
| Asp | Leu | Val | His | Pro | Thr | Val | Thr | Phe | Pro | Asn | Pro | Asn | Ala | His | Leu | |
| | -30 | | | | -25 | | | | | -20 | | | | | | |
| ccc | gtc | gtg | cgc | tcc | acc | cag | ccc | atc | cgg | aac | ctg | acc | gga | cgt | gct | 607 |
| Pro | Val | Val | Arg | Ser | Thr | Gln | Pro | Ile | Arg | Asn | Leu | Thr | Gly | Arg | Ala | |
| -15 | | | | -10 | | | | | -5 | | | | | -1 | 1 | |
| ata | ccg | gcc | tct | tgc | gcg | agc | acc | atc | acc | cct | gcg | tgc | ttg | cag | gcc | 655 |
| Ile | Pro | Ala | Ser | Cys | Ala | Ser | Thr | Ile | Thr | Pro | Ala | Cys | Leu | Gln | Ala | |
| | | | 5 | | | | | 10 | | | | | 15 | | | |
| atc | tac | ggt | atc | ccc | acc | acc | aag | gct | act | cag | tcc | tcg | aac | aag | ctc | 703 |
| Ile | Tyr | Gly | Ile | Pro | Thr | Thr | Lys | Ala | Thr | Gln | Ser | Ser | Asn | Lys | Leu | |
| | | | 20 | | | | 25 | | | | | 30 | | | | |
| gct | gtc | agc | ggc | ttc | atc | gac | cag | ttt | gcg | aac | aag | gct | gac | ctg | aag | 751 |
| Ala | Val | Ser | Gly | Phe | Ile | Asp | Gln | Phe | Ala | Asn | Lys | Ala | Asp | Leu | Lys | |
| | 35 | | | | | 40 | | | | | 45 | | | | | |
| tca | ttc | ctg | gcc | cag | ttc | cgc | aaa | gac | atc | tca | tcc | tcc | acg | act | ttc | 799 |
| Ser | Phe | Leu | Ala | Gln | Phe | Arg | Lys | Asp | Ile | Ser | Ser | Ser | Thr | Thr | Phe | |
| 50 | | | | | 55 | | | | | 60 | | | | | 65 | |
| tcg | ctt | cag | act | ctc | gat | ggt | gga | gag | aac | gac | cag | agc | cct | agc | gag | 847 |
| Ser | Leu | Gln | Thr | Leu | Asp | Gly | Gly | Glu | Asn | Asp | Gln | Ser | Pro | Ser | Glu | |
| | | | 70 | | | | | 75 | | | | | 80 | | | |
| gcg | ggt | atc | gag | gct | aac | ttg | gat | atc | cag | tac | acc | gtc | ggc | ctc | gcc | 895 |
| Ala | Gly | Ile | Glu | Ala | Asn | Leu | Asp | Ile | Gln | Tyr | Thr | Val | Gly | Leu | Ala | |
| | | | 85 | | | | | 90 | | | | | 95 | | | |
| acg | ggc | gtc | cct | acc | acg | ttc | atc | tcc | gtc | ggc | gac | gac | ttc | cag | gat | 943 |
| Thr | Gly | Val | Pro | Thr | Thr | Phe | Ile | Ser | Val | Gly | Asp | Asp | Phe | Gln | Asp | |
| | | 100 | | | | | 105 | | | | | 110 | | | | |
| ggc | aac | ttg | gag | ggc | ttc | ctg | gac | atc | atc | aac | ttc | ttg | ctc | ggc | gag | 991 |
| Gly | Asn | Leu | Glu | Gly | Phe | Leu | Asp | Ile | Ile | Asn | Phe | Leu | Leu | Gly | Glu | |
| | 115 | | | | | 120 | | | | | 125 | | | | | |
| agc | aac | ccg | ccg | cag | gtc | ctc | acc | acc | agt | tac | ggc | cag | aac | gag | aac | 1039 |
| Ser | Asn | Pro | Pro | Gln | Val | Leu | Thr | Thr | Ser | Tyr | Gly | Gln | Asn | Glu | Asn | |
| 130 | | | | | 135 | | | | | 140 | | | | | 145 | |
| acg | atc | tcg | gcc | aag | ctt | gct | aac | caa | ctt | tgc | aat | gcg | tac | gct | cag | 1087 |
| Thr | Ile | Ser | Ala | Lys | Leu | Ala | Asn | Gln | Leu | Cys | Asn | Ala | Tyr | Ala | Gln | |
| | | | | 150 | | | | | 155 | | | | | 160 | | |
| ctc | ggc | gcg | cgc | ggc | acc | tct | atc | ctc | ttc | gcg | tcg | ggt | gat | ggc | ggt | 1135 |
| Leu | Gly | Ala | Arg | Gly | Thr | Ser | Ile | Leu | Phe | Ala | Ser | Gly | Asp | Gly | Gly | |
| | | | 165 | | | | | 170 | | | | | 175 | | | |
| gtg | tcc | ggc | tcg | cag | tcc | gcg | cac | tgc | agc | aat | ttt | gtc | ccg | aca | ttc | 1183 |
| Val | Ser | Gly | Ser | Gln | Ser | Ala | His | Cys | Ser | Asn | Phe | Val | Pro | Thr | Phe | |
| | | 180 | | | | | 185 | | | | | 190 | | | | |
| ccc | tcc | ggc | tgc | ccc | ttc | atg | act | tcc | gtc | ggc | gcg | acg | cag | ggc | gtc | 1231 |
| Pro | Ser | Gly | Cys | Pro | Phe | Met | Thr | Ser | Val | Gly | Ala | Thr | Gln | Gly | Val | |
| | 195 | | | | | 200 | | | | | 205 | | | | | |
| agc | ccc | gag | act | gcc | gcc | gcc | ttc | tca | tcc | ggc | ggc | ttc | tcg | aac | gtg | 1279 |
| Ser | Pro | Glu | Thr | Ala | Ala | Ala | Phe | Ser | Ser | Gly | Gly | Phe | Ser | Asn | Val | |
| 210 | | | | | 215 | | | | | 220 | | | | | 225 | |

```
ttc ggc atc ccg tcg tac cag gct tcc gcg gtc agc ggc tac ctg tcc        1327
Phe Gly Ile Pro Ser Tyr Gln Ala Ser Ala Val Ser Gly Tyr Leu Ser
                230                 235                 240 gcg ctc gga agc acg aac tcg ggc aag ttc aac cgc agc gga cgc gga        1375
Ala Leu Gly Ser Thr Asn Ser Gly Lys Phe Asn Arg Ser Gly Arg Gly
            245                 250                 255 ttc ccc gac gtc tcc acg caa ggc gtg gac ttc cag atc gtc agc ggc        1423
Phe Pro Asp Val Ser Thr Gln Gly Val Asp Phe Gln Ile Val Ser Gly
        260                 265                 270 ggc cag acg atc ggc gtc gac ggc acg agc tgc gcc agc ccg acg ttc        1471
Gly Gln Thr Ile Gly Val Asp Gly Thr Ser Cys Ala Ser Pro Thr Phe
    275                 280                 285 gcg agc gtc atc tcg ctg gta aac gac cgc ctc atc gcg gcc ggc aag        1519
Ala Ser Val Ile Ser Leu Val Asn Asp Arg Leu Ile Ala Ala Gly Lys
290                 295                 300                 305 agc ccg ctc ggc ttc ctg aac ccc ttc ctg tac tcg tcg gcg ggc aag        1567
Ser Pro Leu Gly Phe Leu Asn Pro Phe Leu Tyr Ser Ser Ala Gly Lys
                310                 315                 320 gcc gcg ctc aac gac gtc acg agt ggc tcg aac cct ggc tgc agc acg        1615
Ala Ala Leu Asn Asp Val Thr Ser Gly Ser Asn Pro Gly Cys Ser Thr
            325                 330                 335 aac ggc ttc ccc gct aag gcc ggc tgg gac ccg gtc act ggt ctt ggc        1663
Asn Gly Phe Pro Ala Lys Ala Gly Trp Asp Pro Val Thr Gly Leu Gly
        340                 345                 350 acg ccc aac ttt gcc aag ctc ctc acc gcg gtc ggc ctg tgaatgtgga        1712
Thr Pro Asn Phe Ala Lys Leu Leu Thr Ala Val Gly Leu
    355                 360                 365 cgaaatacaa gaacgtggaa cgatgtgcac agtcagaagg aatgatcgcg cagtggcggt     1772
gtactattgt agatgtacgg gcaaagatgt acaccttttt agcagtcaaa atgtaaacgt     1832
gtttgcgtct ggctt                                                      1847

<210> SEQ ID NO 2
<211> LENGTH: 564
<212> TYPE: PRT
<213> ORGANISM: Meripilus giganteus

<400> SEQUENCE: 2

Met Val Ala Thr  Ser Leu Leu Val  Ala Ser Leu Phe  Thr Leu Ala
                 -195             -190             -185
Leu Gly Thr Pro  Thr Gly Arg Asn  Leu Lys Leu His  Glu Ala Arg
                 -180             -175             -170

Glu Asp Leu Pro  Ala Gly Phe Ser  Leu Arg Gly Ala  Ala Ser Pro
                 -165             -160             -155

Asp Thr Thr Leu  Lys Leu Arg Ile  Ala Leu Val Gln  Asn Asn Phe
                 -150             -145             -140

Ala Glu Leu Glu  Asp Lys Leu Tyr  Asp Val Ser Thr  Pro Ser Ser
                 -135             -130             -125

Ala Asn Tyr Gly  Asn His Leu Ser  Lys Glu Glu Val  Glu Gln Tyr
                 -120             -115             -110

Ile Ala Pro Ala  Pro Glu Ser Val  Lys Ala Val Asn  Ala Trp Leu Thr
                 -105             -100             -95

Glu Asn Gly Leu  Asp Ala His Thr  Ile Ser Pro Ala  Gly Asp Trp Leu
            -90                   -85                  -80

Ala Phe Glu Val  Pro Val Ser Lys  Ala Asn Glu Leu  Phe Asp Ala Asp
        -75                       -70                  -65

Phe Ser Val Phe  Thr His Asp Glu  Ser Gly Leu Glu  Ala Ile Arg Thr
-60                   -55                  -50                  -45

Leu Ala Tyr Ser  Ile Pro Ala Glu  Leu Gln Gly His  Leu Asp Leu Val
                 -40                  -35                  -30
```

```
His Pro Thr Val Thr Phe Pro Asn Pro Asn Ala His Leu Pro Val Val
        -25                 -20                 -15

Arg Ser Thr Gln Pro Ile Arg Asn Leu Thr Gly Arg Ala Ile Pro Ala
        -10                  -5                  -1   1

Ser Cys Ala Ser Thr Ile Thr Pro Ala Cys Leu Gln Ala Ile Tyr Gly
 5               10                  15                       20

Ile Pro Thr Thr Lys Ala Thr Gln Ser Ser Asn Lys Leu Ala Val Ser
                 25                  30                  35

Gly Phe Ile Asp Gln Phe Ala Asn Lys Ala Asp Leu Lys Ser Phe Leu
             40                  45                  50

Ala Gln Phe Arg Lys Asp Ile Ser Ser Thr Thr Phe Ser Leu Gln
             55                  60                  65

Thr Leu Asp Gly Gly Glu Asn Asp Gln Ser Pro Ser Glu Ala Gly Ile
     70                  75                  80

Glu Ala Asn Leu Asp Ile Gln Tyr Thr Val Gly Leu Ala Thr Gly Val
 85              90                  95                      100

Pro Thr Thr Phe Ile Ser Val Gly Asp Asp Phe Gln Asp Gly Asn Leu
                105                 110                     115

Glu Gly Phe Leu Asp Ile Ile Asn Phe Leu Leu Gly Glu Ser Asn Pro
             120                 125                 130

Pro Gln Val Leu Thr Thr Ser Tyr Gly Gln Asn Glu Asn Thr Ile Ser
             135                 140                 145

Ala Lys Leu Ala Asn Gln Leu Cys Asn Ala Tyr Ala Gln Leu Gly Ala
         150                 155                 160

Arg Gly Thr Ser Ile Leu Phe Ala Ser Gly Asp Gly Val Ser Gly
165             170                 175                     180

Ser Gln Ser Ala His Cys Ser Asn Phe Val Pro Thr Phe Pro Ser Gly
             185                 190                 195

Cys Pro Phe Met Thr Ser Val Gly Ala Thr Gln Gly Val Ser Pro Glu
             200                 205                 210

Thr Ala Ala Ala Phe Ser Ser Gly Gly Phe Ser Asn Val Phe Gly Ile
         215                 220                 225

Pro Ser Tyr Gln Ala Ser Ala Val Ser Gly Tyr Leu Ser Ala Leu Gly
         230                 235                 240

Ser Thr Asn Ser Gly Lys Phe Asn Arg Ser Gly Arg Gly Phe Pro Asp
245                 250                 255                 260

Val Ser Thr Gln Gly Val Asp Phe Gln Ile Val Ser Gly Gly Gln Thr
                 265                 270                 275

Ile Gly Val Asp Gly Thr Ser Cys Ala Ser Pro Thr Phe Ala Ser Val
             280                 285                 290

Ile Ser Leu Val Asn Asp Arg Leu Ile Ala Ala Gly Lys Ser Pro Leu
         295                 300                 305

Gly Phe Leu Asn Pro Phe Leu Tyr Ser Ser Ala Gly Lys Ala Ala Leu
     310                 315                 320

Asn Asp Val Thr Ser Gly Ser Asn Pro Gly Cys Ser Thr Asn Gly Phe
325                 330                 335                 340

Pro Ala Lys Ala Gly Trp Asp Pro Val Thr Gly Leu Gly Thr Pro Asn
             345                 350                 355

Phe Ala Lys Leu Leu Thr Ala Val Gly Leu
             360                 365

<210> SEQ ID NO 3
<211> LENGTH: 1719
```

```
<212> TYPE: DNA
<213> ORGANISM: Artificial sequence
<220> FEATURE:
<223> OTHER INFORMATION: Synthetic construct
<220> FEATURE:
<221> NAME/KEY: CDS
<222> LOCATION: (1)..(1716)
<220> FEATURE:
<221> NAME/KEY: mat_peptide
<222> LOCATION: (595)..(1692)
<220> FEATURE:
<221> NAME/KEY: misc_recomb
<222> LOCATION: (1693)..(1716)

<400> SEQUENCE: 3
```

| | | | | | | | | | | | | | | |
|---|---|---|---|---|---|---|---|---|---|---|---|---|---|---|
| atg | gtc | gcc | acc | agc | ttg | ctc | gtt | gcc | tcc | cta | ttc | acg | ctc | gcc | 45 |
| Met | Val | Ala | Thr | Ser | Leu | Leu | Val | Ala | Ser | Leu | Phe | Thr | Leu | Ala | |
| | | | -195 | | | | -190 | | | | -185 | | | | |
| ctc | ggc | acg | ccg | acg | ggt | cgc | aac | ctc | aag | ctg | cac | gag | gcg | cgc | 90 |
| Leu | Gly | Thr | Pro | Thr | Gly | Arg | Asn | Leu | Lys | Leu | His | Glu | Ala | Arg | |
| | | | -180 | | | | -175 | | | | -170 | | | | |
| gaa | gac | ctt | cct | gcc | ggt | ttc | tcg | ctg | cgc | ggc | gcc | gcc | tcg | ccc | 135 |
| Glu | Asp | Leu | Pro | Ala | Gly | Phe | Ser | Leu | Arg | Gly | Ala | Ala | Ser | Pro | |
| | | | -165 | | | | -160 | | | | -155 | | | | |
| gac | acg | acg | ctg | aag | ctc | cgc | atc | gcg | ctc | gtg | cag | aac | aac | ttc | 180 |
| Asp | Thr | Thr | Leu | Lys | Leu | Arg | Ile | Ala | Leu | Val | Gln | Asn | Asn | Phe | |
| | | | -150 | | | | -145 | | | | -140 | | | | |
| gcc | gag | ctc | gaa | gac | aag | ctc | tac | gac | gtc | agc | aca | ccg | tcc | agc | 225 |
| Ala | Glu | Leu | Glu | Asp | Lys | Leu | Tyr | Asp | Val | Ser | Thr | Pro | Ser | Ser | |
| | | | -135 | | | | -130 | | | | -125 | | | | |
| gcc | aac | tac | ggc | aac | cac | ctc | tcg | aag | gaa | gag | gtt | gag | cag | tac | 270 |
| Ala | Asn | Tyr | Gly | Asn | His | Leu | Ser | Lys | Glu | Glu | Val | Glu | Gln | Tyr | |
| | | | -120 | | | | -115 | | | | -110 | | | | |
| att | gct | ccg | gct | ccc | gag | agc | gtg | aaa | gcc | gtg | aat | gcc | tgg | ctc | acc | 318 |
| Ile | Ala | Pro | Ala | Pro | Glu | Ser | Val | Lys | Ala | Val | Asn | Ala | Trp | Leu | Thr |
| | | | -105 | | | | -100 | | | | -95 | | | | |
| gag | aac | gga | ctc | gac | gcg | cac | acc | att | tcg | ccc | gcc | ggc | gac | tgg | ctc | 366 |
| Glu | Asn | Gly | Leu | Asp | Ala | His | Thr | Ile | Ser | Pro | Ala | Gly | Asp | Trp | Leu |
| | | -90 | | | | -85 | | | | | -80 | | | | |
| gca | ttc | gag | gtc | ccc | gtc | agc | aag | gcg | aat | gag | ctc | ttc | gac | gcc | gac | 414 |
| Ala | Phe | Glu | Val | Pro | Val | Ser | Lys | Ala | Asn | Glu | Leu | Phe | Asp | Ala | Asp |
| | -75 | | | | | -70 | | | | | -65 | | | | |
| ttc | tcc | gtg | ttt | acc | cac | gat | gag | tcc | ggc | ctc | gag | gct | atc | cgg | acg | 462 |
| Phe | Ser | Val | Phe | Thr | His | Asp | Glu | Ser | Gly | Leu | Glu | Ala | Ile | Arg | Thr |
| -60 | | | | | -55 | | | | | -50 | | | | | -45 |
| ctg | gcc | tac | tcc | atc | cct | gct | gag | ctt | cag | gga | cac | ctc | gac | ctt | gtt | 510 |
| Leu | Ala | Tyr | Ser | Ile | Pro | Ala | Glu | Leu | Gln | Gly | His | Leu | Asp | Leu | Val |
| | | | -40 | | | | -35 | | | | | -30 | | | | |
| cac | ccc | acc | gtc | acg | ttc | ccg | aac | ccc | aat | gcg | cac | ctg | ccc | gtc | gtg | 558 |
| His | Pro | Thr | Val | Thr | Phe | Pro | Asn | Pro | Asn | Ala | His | Leu | Pro | Val | Val |
| | | -25 | | | | | -20 | | | | | -15 | | | | |
| cgc | tcc | acc | cag | ccc | atc | cgg | aac | ctg | acc | gga | cgt | gct | ata | ccg | gcc | 606 |
| Arg | Ser | Thr | Gln | Pro | Ile | Arg | Asn | Leu | Thr | Gly | Arg | Ala | Ile | Pro | Ala |
| | | -10 | | | | | -5 | | | | -1 | 1 | | | | |
| tct | tgc | gcg | agc | acc | atc | acc | cct | gcg | tgc | ttg | cag | gcc | atc | tac | ggt | 654 |
| Ser | Cys | Ala | Ser | Thr | Ile | Thr | Pro | Ala | Cys | Leu | Gln | Ala | Ile | Tyr | Gly |
| 5 | | | | | 10 | | | | | 15 | | | | | 20 |
| atc | ccc | acc | acc | aag | gct | act | cag | tcc | tcg | aac | aag | ctc | gct | gtc | agc | 702 |
| Ile | Pro | Thr | Thr | Lys | Ala | Thr | Gln | Ser | Ser | Asn | Lys | Leu | Ala | Val | Ser |
| | | | | 25 | | | | | 30 | | | | | 35 | |
| ggc | ttc | atc | gac | cag | ttt | gcg | aac | aag | gct | gac | ctg | aag | tca | ttc | ctg | 750 |
| Gly | Phe | Ile | Asp | Gln | Phe | Ala | Asn | Lys | Ala | Asp | Leu | Lys | Ser | Phe | Leu |
| | | 40 | | | | | 45 | | | | | 50 | | | | |

```
gcc cag ttc cgc aaa gac atc tca tcc tcc acg act ttc tcg ctt cag    798
Ala Gln Phe Arg Lys Asp Ile Ser Ser Ser Thr Thr Phe Ser Leu Gln
         55                  60                  65 act ctc gat ggt gga gag aac gac cag agc cct agc gag gcg ggt atc    846
Thr Leu Asp Gly Gly Glu Asn Asp Gln Ser Pro Ser Glu Ala Gly Ile
 70                  75                  80 gag gct aac ttg gat atc cag tac acc gtc ggc ctc gcc acg ggc gtc    894
Glu Ala Asn Leu Asp Ile Gln Tyr Thr Val Gly Leu Ala Thr Gly Val
 85                  90                  95                 100 cct acc acg ttc atc tcc gtc ggc gac gac ttc cag gat ggc aac ttg    942
Pro Thr Thr Phe Ile Ser Val Gly Asp Asp Phe Gln Asp Gly Asn Leu
                105                 110                 115 gag ggc ttc ctg gac atc atc aac ttc ttg ctc ggc gag agc aac ccg    990
Glu Gly Phe Leu Asp Ile Ile Asn Phe Leu Leu Gly Glu Ser Asn Pro
                120                 125                 130 ccg cag gtc ctc acc acc agt tac ggc cag aac gag aac acg atc tcg   1038
Pro Gln Val Leu Thr Thr Ser Tyr Gly Gln Asn Glu Asn Thr Ile Ser
                135                 140                 145 gcc aag ctt gct aac caa ctt tgc aat gcg tac gct cag ctc ggc gcg   1086
Ala Lys Leu Ala Asn Gln Leu Cys Asn Ala Tyr Ala Gln Leu Gly Ala
150                 155                 160 cgc ggc acc tct atc ctc ttc gcg tcg ggt gat ggc ggt gtg tcc ggc   1134
Arg Gly Thr Ser Ile Leu Phe Ala Ser Gly Asp Gly Gly Val Ser Gly
165                 170                 175                 180 tcg cag tcc gcg cac tgc agc aat ttt gtc ccg aca ttc ccc tcc ggc   1182
Ser Gln Ser Ala His Cys Ser Asn Phe Val Pro Thr Phe Pro Ser Gly
                185                 190                 195 tgc ccc ttc atg act tcc gtc ggc gcg acg cag ggc gtc agc ccc gag   1230
Cys Pro Phe Met Thr Ser Val Gly Ala Thr Gln Gly Val Ser Pro Glu
                200                 205                 210 act gcc gcc gcc ttc tca tcc ggc ggc ttc tcg aac gtg ttc ggc atc   1278
Thr Ala Ala Ala Phe Ser Ser Gly Gly Phe Ser Asn Val Phe Gly Ile
                215                 220                 225 ccg tcg tac cag gct tcc gcg gtc agc ggc tac ctg tcc gcg ctc gga   1326
Pro Ser Tyr Gln Ala Ser Ala Val Ser Gly Tyr Leu Ser Ala Leu Gly
230                 235                 240 agc acg aac tcg ggc aag ttc aac cgc agc gga cgc gga ttc ccc gac   1374
Ser Thr Asn Ser Gly Lys Phe Asn Arg Ser Gly Arg Gly Phe Pro Asp
245                 250                 255                 260 gtc tcc acg caa ggc gtg gac ttc cag atc gtc agc ggc ggc cag acg   1422
Val Ser Thr Gln Gly Val Asp Phe Gln Ile Val Ser Gly Gly Gln Thr
                265                 270                 275 atc ggc gtc gac ggc acg agc tgc gcc agc ccg acg ttc gcg agc gtc   1470
Ile Gly Val Asp Gly Thr Ser Cys Ala Ser Pro Thr Phe Ala Ser Val
                280                 285                 290 atc tcg ctg gta aac gac cgc ctc atc gcg gcc ggc aag agc ccg ctc   1518
Ile Ser Leu Val Asn Asp Arg Leu Ile Ala Ala Gly Lys Ser Pro Leu
                295                 300                 305 ggc ttc ctg aac ccc ttc ctg tac tcg tcg gcg ggc aag gcc gcg ctc   1566
Gly Phe Leu Asn Pro Phe Leu Tyr Ser Ser Ala Gly Lys Ala Ala Leu
                310                 315                 320 aac gac gtc acg agt ggc tcg aac cct ggc tgc agc acg aac ggc ttc   1614
Asn Asp Val Thr Ser Gly Ser Asn Pro Gly Cys Ser Thr Asn Gly Phe
325                 330                 335                 340 ccc gct aag gcc ggc tgg gac ccg gtc act ggt ctt ggc acg ccc aac   1662
Pro Ala Lys Ala Gly Trp Asp Pro Val Thr Gly Leu Gly Thr Pro Asn
                345                 350                 355 ttt gcc aag ctc ctc acc gcg gtc ggc ctg cga cat cag cac cag cat   1710
Phe Ala Lys Leu Leu Thr Ala Val Gly Leu Arg His Gln His Gln His
```

```
                  360             365             370
cag cac tga                                                         1719
Gln His <210> SEQ ID NO 4
<211> LENGTH: 572
<212> TYPE: PRT
<213> ORGANISM: Artificial sequence
<220> FEATURE:
<223> OTHER INFORMATION: Synthetic Construct

<400> SEQUENCE: 4

Met Val Ala Thr Ser Leu Leu Val Ala Ser Leu Phe Thr Leu Ala
             -195            -190             -185
Leu Gly Thr Pro Thr Gly Arg Asn Leu Lys Leu His Glu Ala Arg
             -180            -175             -170

Glu Asp Leu Pro Ala Gly Phe Ser Leu Arg Gly Ala Ala Ser Pro
             -165            -160             -155

Asp Thr Thr Leu Lys Leu Arg Ile Ala Leu Val Gln Asn Asn Phe
             -150            -145             -140

Ala Glu Leu Glu Asp Lys Leu Tyr Asp Val Ser Thr Pro Ser Ser
             -135            -130             -125

Ala Asn Tyr Gly Asn His Leu Ser Lys Glu Glu Val Glu Gln Tyr
             -120            -115             -110

Ile Ala Pro Ala Pro Glu Ser Val Lys Ala Val Asn Ala Trp Leu Thr
             -105            -100             -95

Glu Asn Gly Leu Asp Ala His Thr Ile Ser Pro Ala Gly Asp Trp Leu
         -90             -85              -80

Ala Phe Glu Val Pro Val Ser Lys Ala Asn Glu Leu Phe Asp Ala Asp
     -75             -70              -65

Phe Ser Val Phe Thr His Asp Glu Ser Gly Leu Glu Ala Ile Arg Thr
-60             -55              -50              -45

Leu Ala Tyr Ser Ile Pro Ala Glu Leu Gln Gly His Leu Asp Leu Val
                -40             -35              -30

His Pro Thr Val Thr Phe Pro Asn Pro Asn Ala His Leu Pro Val Val
                -25             -20              -15

Arg Ser Thr Gln Pro Ile Arg Asn Leu Thr Gly Arg Ala Ile Pro Ala
         -10              -5              -1   1

Ser Cys Ala Ser Thr Ile Thr Pro Ala Cys Leu Gln Ala Ile Tyr Gly
5                10              15              20

Ile Pro Thr Thr Lys Ala Thr Gln Ser Ser Asn Lys Leu Ala Val Ser
                25              30              35

Gly Phe Ile Asp Gln Phe Ala Asn Lys Ala Asp Leu Lys Ser Phe Leu
                40              45              50

Ala Gln Phe Arg Lys Asp Ile Ser Ser Thr Thr Phe Ser Leu Gln
         55              60              65

Thr Leu Asp Gly Gly Glu Asn Asp Gln Ser Pro Ser Glu Ala Gly Ile
     70              75              80

Glu Ala Asn Leu Asp Ile Gln Tyr Thr Val Gly Leu Ala Thr Gly Val
85              90              95              100

Pro Thr Thr Phe Ile Ser Val Gly Asp Asp Phe Gln Asp Gly Asn Leu
                105             110             115

Glu Gly Phe Leu Asp Ile Ile Asn Phe Leu Leu Gly Glu Ser Asn Pro
                120             125             130

Pro Gln Val Leu Thr Thr Ser Tyr Gly Gln Asn Glu Asn Thr Ile Ser
         135             140             145
```

```
Ala Lys Leu Ala Asn Gln Leu Cys Asn Ala Tyr Ala Gln Leu Gly Ala
            150                 155                 160

Arg Gly Thr Ser Ile Leu Phe Ala Ser Gly Asp Gly Val Ser Gly
165                 170                 175                 180

Ser Gln Ser Ala His Cys Ser Asn Phe Val Pro Thr Phe Pro Ser Gly
                185                 190                 195

Cys Pro Phe Met Thr Ser Val Gly Ala Thr Gln Gly Val Ser Pro Glu
                200                 205                 210

Thr Ala Ala Ala Phe Ser Ser Gly Gly Phe Ser Asn Val Phe Gly Ile
                215                 220                 225

Pro Ser Tyr Gln Ala Ser Ala Val Ser Gly Tyr Leu Ser Ala Leu Gly
            230                 235                 240

Ser Thr Asn Ser Gly Lys Phe Asn Arg Ser Gly Arg Gly Phe Pro Asp
245                 250                 255                 260

Val Ser Thr Gln Gly Val Asp Phe Gln Ile Val Ser Gly Gly Gln Thr
                265                 270                 275

Ile Gly Val Asp Gly Thr Ser Cys Ala Ser Pro Thr Phe Ala Ser Val
                280                 285                 290

Ile Ser Leu Val Asn Asp Arg Leu Ile Ala Ala Gly Lys Ser Pro Leu
            295                 300                 305

Gly Phe Leu Asn Pro Phe Leu Tyr Ser Ser Ala Gly Lys Ala Ala Leu
310                 315                 320

Asn Asp Val Thr Ser Gly Ser Asn Pro Gly Cys Ser Thr Asn Gly Phe
325                 330                 335                 340

Pro Ala Lys Ala Gly Trp Asp Pro Val Thr Gly Leu Gly Thr Pro Asn
                345                 350                 355

Phe Ala Lys Leu Leu Thr Ala Val Gly Leu Arg His Gln His Gln His
                360                 365                 370

Gln His

<210> SEQ ID NO 5
<211> LENGTH: 366
<212> TYPE: PRT
<213> ORGANISM: Meripilus giganteus

<400> SEQUENCE: 5

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
                20                  25                  30

Leu Ala Val Ser Gly Phe Ile Asp Gln Phe Ala Asn Lys Ala Asp Leu
            35                  40                  45

Lys Ser Phe Leu Ala Gln Phe Arg Lys Asp Ile Ser Ser Ser Thr Thr
50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
                100                 105                 110

Asp Gly Asn Leu Glu Gly Phe Leu Asp Ile Ile Asn Phe Leu Leu Gly
            115                 120                 125

Glu Ser Asn Pro Pro Gln Val Leu Thr Thr Ser Tyr Gly Gln Asn Glu
            130                 135                 140
```

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
                260                 265                 270

Gly Gly Gln Thr Ile Gly Val Asp Gly Thr Ser Cys Ala Ser Pro Thr
            275                 280                 285

Phe Ala Ser Val Ile Ser Leu Val Asn Asp Arg Leu Ile Ala Ala Gly
        290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
                340                 345                 350

Gly Thr Pro Asn Phe Ala Lys Leu Leu Thr Ala Val Gly Leu
            355                 360                 365

<210> SEQ ID NO 6
<211> LENGTH: 371
<212> TYPE: PRT
<213> ORGANISM: Artificial sequence
<220> FEATURE:
<223> OTHER INFORMATION: Synthetic construct

<400> SEQUENCE: 6

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
                20                  25                  30

Leu Ala Val Ser Gly Phe Ile Asp Gln Phe Ala Asn Lys Ala Asp Leu
            35                  40                  45

Lys Ser Phe Leu Ala Gln Phe Arg Lys Asp Ile Ser Ser Ser Thr Thr
50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
        115                 120                 125

Glu Ser Asn Pro Pro Gln Val Leu Thr Thr Ser Tyr Gly Gln Asn Glu
    130                 135                 140

```
Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
        195                 200                 205

Val Ser Pro Glu Thr Ala Ala Ala Phe Ser Ser Gly Gly Phe Ser Asn
    210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
                260                 265                 270

Gly Gly Gln Thr Ile Gly Val Asp Gly Thr Ser Cys Ala Ser Pro Thr
            275                 280                 285

Phe Ala Ser Val Ile Ser Leu Val Asn Asp Arg Leu Ile Ala Ala Gly
        290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
                340                 345                 350

Gly Thr Pro Asn Phe Ala Lys Leu Leu Thr Ala Val Gly Leu Arg His
                355                 360                 365

Gln His Gln
        370

<210> SEQ ID NO 7
<211> LENGTH: 30
<212> TYPE: DNA
<213> ORGANISM: Artificial sequence
<220> FEATURE:
<223> OTHER INFORMATION: Primer 567

<400> SEQUENCE: 7
tagggatcct cacgatggtc gccaccagct                                    30

<210> SEQ ID NO 8
<211> LENGTH: 18
<212> TYPE: DNA
<213> ORGANISM: Artificial sequence
<220> FEATURE:
<223> OTHER INFORMATION: Primer 598

<400> SEQUENCE: 8
caggccgacc gcggtgag                                                 18
```

UNITED STATES PATENT AND TRADEMARK OFFICE
CERTIFICATE OF CORRECTION

PATENT NO. : 10,308,967 B2
APPLICATION NO. : 15/033751
DATED : June 4, 2019
INVENTOR(S) : Long et al.

Page 1 of 1

It is certified that error appears in the above-identified patent and that said Letters Patent is hereby corrected as shown below:

In the Claims

In Claim 2, Line 1 (Column 63), (Line 4) please delete "said".

In Claim 7, Line 3 (Column 63), (Line 24) please delete "hemicelluase" and insert --hemicellulase--.

Signed and Sealed this
Tenth Day of September, 2019

Andrei Iancu
*Director of the United States Patent and Trademark Office*